US006939569B1

(12) United States Patent
Green et al.

(10) Patent No.: US 6,939,569 B1
(45) Date of Patent: Sep. 6, 2005

(54) MEDICAL DEVICE HAVING ANTI-INFECTIVE AND CONTRACEPTIVE PROPERTIES

(75) Inventors: Terrence R. Green, Lake Oswego, OR (US); Jack Fellman, McMinnville, OR (US)

(73) Assignee: Oxibio, Inc., Portland, OR (US)

( * ) Notice: Subject to any disclaimer, the term of this patent is extended or adjusted under 35 U.S.C. 154(b) by 0 days.

(21) Appl. No.: 09/336,392

(22) Filed: Jun. 18, 1999

Related U.S. Application Data

(63) Continuation-in-part of application No. 09/265,196, filed on Mar. 10, 1999, now abandoned, and a continuation-in-part of application No. 09/179,233, filed on Oct. 26, 1998.

(60) Provisional application No. 60/090,014, filed on Jun. 19, 1998.

(51) Int. Cl.[7] ............... A61K 33/08; A61K 31/19; A61K 33/40; A01N 25/00
(52) U.S. Cl. ............... 424/667; 424/405; 424/409; 424/422; 424/423; 424/486; 424/668; 424/669; 424/670; 424/671; 514/557; 514/772.3; 514/953
(58) Field of Search ............... 424/667, 448, 424/449, 405, 409, 422, 423, 486, 607, 613, 424/661, 668, 669, 670, 718, 671; 2/161.7; 514/552, 557, 772.3, 953

(56) References Cited

U.S. PATENT DOCUMENTS

| 1,867,222 A | * | 7/1932 | Karns | |
|---|---|---|---|---|
| 2,355,231 A | | 8/1944 | Moore | 205/701 |
| 3,235,446 A | | 2/1966 | Shelanski et al. | |
| 4,010,141 A | | 3/1977 | Onozuka et al. | 260/45.75 K |
| 4,012,221 A | | 3/1977 | Walker et al. | 71/66 |
| 4,012,347 A | | 3/1977 | Gitlitz et al. | 260/27 R |
| 4,093,610 A | | 6/1978 | Abraham et al. | 260/112.5 |
| 4,166,111 A | | 8/1979 | Cardarelli | 424/78 |
| 4,228,614 A | | 10/1980 | Cardarelli | 43/131 |
| 4,237,113 A | | 12/1980 | Cardarelli | 424/78 |
| 4,237,114 A | | 12/1980 | Cardarelli | 424/78 |
| 4,278,548 A | | 7/1981 | Bettinger et al. | 210/636 |
| 4,311,543 A | | 1/1982 | Strickman et al. | 156/224 |
| 4,312,833 A | | 1/1982 | Clough et al. | 422/30 |
| 4,326,510 A | | 4/1982 | Buckles | 128/127 |
| 4,381,380 A | | 4/1983 | LeVeen et al. | 525/452 |
| 4,446,860 A | | 5/1984 | Gutnick | 128/132 |
| 4,476,108 A | | 10/1984 | Kessler et al. | 424/50 |
| 4,526,578 A | | 7/1985 | Wong | 604/892 |
| 4,542,169 A | | 9/1985 | Costerton | 523/121 |
| 4,553,972 A | | 11/1985 | Vickery | 604/892 |
| 4,576,817 A | * | 3/1986 | Montgomery et al. | 424/94 |
| 4,585,451 A | | 4/1986 | Millar | 604/892 |
| 4,707,362 A | | 11/1987 | Nuwayser | 424/433 |
| 4,755,378 A | | 7/1988 | Buxton et al. | 424/80 |
| 4,769,013 A | | 9/1988 | Lorenz et al. | 604/265 |
| 4,832,052 A | | 5/1989 | Mohajer | 128/839 |
| 4,853,978 A | | 8/1989 | Stockum | 2/167 |
| 4,922,928 A | | 5/1990 | Burnhill | 128/832 |
| 4,937,072 A | | 6/1990 | Kessler et al. | 424/94.4 |
| 4,959,216 A | | 9/1990 | Daunter | 424/430 |
| 4,961,931 A | | 10/1990 | Wong | 424/430 |
| 4,983,393 A | | 1/1991 | Cohen et al. | 424/430 |
| 5,000,749 A | | 3/1991 | LeVeen et al. | 604/904 |
| 5,002,540 A | | 3/1991 | Brodman et al. | 604/285 |
| 5,019,096 A | | 5/1991 | Fox, Jr. et al. | 623/1 |
| 5,044,376 A | | 9/1991 | Shields | 128/837 |
| 5,070,889 A | | 12/1991 | LeVeen et al. | 128/830 |
| 5,128,136 A | | 7/1992 | Bentley et al. | 424/443 |
| 5,156,164 A | | 10/1992 | LeVeen et al. | 128/832 |
| 5,224,493 A | | 7/1993 | Sawan et al. | 128/832 |
| 5,227,161 A | | 7/1993 | Kessler | 424/94.4 |
| 5,231,992 A | | 8/1993 | Leon | 128/759 |
| 5,232,914 A | | 8/1993 | Fellman | 514/23 |
| 5,236,703 A | | 8/1993 | Usala | 424/78.36 |
| 5,238,679 A | | 8/1993 | Cyprien et al. | 424/78.25 |
| 5,295,978 A | | 3/1994 | Fan et al. | 604/265 |
| 5,302,392 A | | 4/1994 | Karakelle et al. | 424/409 |
| 5,344,411 A | | 9/1994 | Domb et al. | 604/265 |
| 5,357,636 A | | 10/1994 | Dangman et al. | |
| 5,370,815 A | | 12/1994 | Kessler | 252/106 |
| 5,409,697 A | | 4/1995 | Gluck | 424/78.25 |
| 5,411,550 A | | 5/1995 | Herweck et al. | 623/1.27 |
| 5,419,816 A | | 5/1995 | Sampson et al. | 205/556 |
| 5,419,902 A | | 5/1995 | Kessler | 424/94.4 |
| 5,437,656 A | | 8/1995 | Shikani et al. | 604/89.1 |

(Continued)

FOREIGN PATENT DOCUMENTS

EP 0747062 12/1996

(Continued)

OTHER PUBLICATIONS

Zanowiak "Pharmaceuticals" Kirk-Othmer 1996.*

(Continued)

*Primary Examiner*—S. Mark Clardy
*Assistant Examiner*—Frank Choi
(74) *Attorney, Agent, or Firm*—Heller Ehrman LLP

(57) ABSTRACT

There is disclosed a medical device for implantation that acts to prevent transmission of infectious agents. Specifically, the present invention provides implantable devices, such as catheters or living skin matrices or wound dressings, for insertion into various body cavities or over wound sites to confer to the site microbicidal or virucidal activity. Devices in the disclosure designed as vaginal inserts also exhibit contraceptive spermicidal activity. The coated devices or devices having the inventive polymeric material interspersed throughout are formed into appropriate shapes according to their contemplated uses (such as catheters or Foley catheters). Further, the present invention provides devices for providing therapeutic anti-microbial activity into an infected body cavity or on an infected wound site.

30 Claims, 10 Drawing Sheets

U.S. PATENT DOCUMENTS

| | | | |
|---|---|---|---|
| 5,447,505 A | 9/1995 | Valentine et al. | 604/304 |
| 5,462,713 A | 10/1995 | Schlitzer et al. | 422/37 |
| 5,466,463 A | 11/1995 | Ford | 424/433 |
| 5,492,911 A | 2/1996 | Stief | |
| 5,512,055 A | 4/1996 | Domb et al. | 604/265 |
| 5,545,401 A | 8/1996 | Shanbrom | 424/78.07 |
| 5,558,881 A | 9/1996 | Corby | 424/672 |
| 5,562,652 A | 10/1996 | Davis | 604/890.1 |
| 5,571,535 A | 11/1996 | Flowers et al. | 424/489 |
| 5,577,514 A | 11/1996 | Zimmerman | 128/844 |
| 5,591,350 A | 1/1997 | Piechocki et al. | 210/764 |
| 5,592,949 A | 1/1997 | Moench et al. | 128/837 |
| 5,605,696 A | 2/1997 | Eury et al. | 424/423 |
| 5,607,681 A | 3/1997 | Galley et al. | 424/405 |
| 5,609,866 A | 3/1997 | Khan et al. | 424/78.25 |
| 5,617,877 A | 4/1997 | Moench et al. | 128/837 |
| 5,618,799 A | 4/1997 | Inagi et al. | 514/53 |
| 5,629,024 A | 5/1997 | Kessler et al. | 424/667 |
| 5,639,452 A | 6/1997 | Messier | 424/78.1 |
| 5,648,075 A | 7/1997 | Kessler et al. | 424/94.4 |
| 5,667,492 A | 9/1997 | Bologna et al. | 604/57 |
| 5,679,399 A | 10/1997 | Shlenker et al. | 427/2.3 |
| 5,695,458 A | 12/1997 | Shikani et al. | 604/4 |
| 5,698,738 A | 12/1997 | Garfield et al. | |
| 5,705,050 A | 1/1998 | Sampson et al. | 205/687 |
| 5,747,058 A | 5/1998 | Tipton et al. | 424/423 |
| 5,762,638 A | 6/1998 | Shikani et al. | 604/265 |
| 5,772,971 A | 6/1998 | Murphy et al. | 422/292 |
| 5,810,755 A | 9/1998 | LeVeen et al. | 602/48 |
| 5,819,742 A | 10/1998 | Sokal et al. | 128/830 |
| 5,849,241 A | 12/1998 | Connan | 264/529 |
| 5,885,592 A | 3/1999 | Duan et al. | 424/400 |
| 5,948,385 A | 9/1999 | Chapman et al. | 424/1.29 |
| 5,951,458 A | 9/1999 | Hastings et al. | 600/3 |
| 5,965,276 A | 10/1999 | Shlenker et al. | 428/492 |
| 5,968,542 A | 10/1999 | Tipton et al. | 424/423 |
| 5,994,444 A * | 11/1999 | Trescony et al. | 524/429 |
| 5,997,468 A | 12/1999 | Wolff et al. | 600/36 |
| 6,482,309 B1 | 11/2002 | Green et al. | 205/619 |
| 6,592,890 B1 | 7/2003 | Green et al. | 424/447 |

FOREIGN PATENT DOCUMENTS

| | | |
|---|---|---|
| GB | 0382572 | 10/1932 |
| JP | XP002118134 | 12/1984 |
| WO | 8502422 | 6/1985 |
| WO | WO 93/24132 | 12/1993 |
| WO | WO 94/26317 | 11/1994 |
| WO | WO 95/07691 | 3/1995 |
| WO | 9512316 | 5/1995 |
| WO | 9620019 | 7/1996 |
| WO | 9638548 | 12/1996 |
| WO | WO 98/05689 | 2/1998 |
| WO | 9965538 | 12/1999 |
| WO | 0054593 | 9/2000 |
| WO | 0074743 | 12/2000 |
| WO | 0128598 | 4/2001 |
| WO | 0128600 | 4/2001 |

OTHER PUBLICATIONS

Barabas et al. "Povidone-Iodine" *Analytical Profiles of Drug Substances and Excipients* 25:341-462 (1998).

Caufiled et al. "In Vitro Susceptibility of *Streptococcus mutans* 6715 to Iodine and Sodium Fluoride, Singly and in Combination, at Various pH Values" *Antimicrobial Agents and Chemotherapy* 22(1):115-119 (Jul. 1982).

Conn et al. "Iodine Disinfection of Hydrophilic Contact Lenses" *Annals of Ophthalmology* (Mar. 1981).

Houang et al. "Absence of Bacterial Resistance to Povidone Iodine" *J. Clin. Path.* 29:752-755 (1976).

King et al. "Disinfection properties of some bovine teat dips" *J. Dairy Research* 44:47-55 (1977).

LeVeen et al. "The Mythology of Povidone-Iodine and the Development of Self-Sterilizing Plastics" *SURGERY* 176: 183-190 (Feb. 1993).

Philpott et al. "Selective Cytotoxicity of Hapten-Substituted Cells with an Antibody-Enzyme Conjugate" *Journal of Immunology* 111(3):921-929 (Sep. 1973).

Philpott et al. "Selective Iodination and Cytotoxicity of Tumor Cells with an Antibody-Enzyme Conjugate" *SURGERY* 74(1):51-58 (Jul. 1973).

Pommier et al. "Enzymatic Iodination of Protein Kinetics of Iodine Formation and Protein Iodination Catalyized by Horse-Radish Peroxidase" *European Journal of Biochemistry* 38(3):497-506 (1973).

Rodeheaver et al. "Pharmacokinetics of a New Skin Wound Cleanser" *Amer. J. Surg.* 132:67-74 (Jul. 1976).

Schenkein et al. "The Use of Glucose Oxidase as a Generator of $H_2O_2$ in the Enzymatic Radioiodination of Components of Cell Surfaces" *Cellular Immunology* 5:490-493 (1972).

Shikani et al. "Polymer-Iodine Inactivation of the Human Immunodeficiency Virus" *Journal of the American College of Surgeons* 183:195-200 (Sep. 1996).

Tyagi et al. "Preparation and Antibacterial Evaluation of Urinary Balloon Catheter" *ISA* Paper #97-040 1054(003): 240-245 (Feb. 1997).

"Proceedings of the Second Asian Pacific Congress on Antisepsis" *Postgraduate Medical Journal* 69(3):S1-S134 (1993).

"Proceedings of the Third Asian Pacific Congress on Antisepsis" *Dermatology* 195(2):1-159 (1997).

* cited by examiner

Figure 1. Sustained release of NaI from silicone fabricated device submerged and continuously washed in 10 mM sodium phosphate, 150 mM NaCl, pH 5.6 (see Example 1).

Figure 2. Kinetic release of encapsulated $I_2O_5$ from silicone fabricated device at various intervals after submersion in 100 mM sodium citrate, pH 4.0, at 2% and 10% $I_2O_5$ formulations by mass (see Example 3).

Figure 3. Recovery of I- and IO$_3$- at varying intervals following submersion of silicone fabricated device in 100 mM sodium citrate, pH 4.0, in a formulation consisting of 2% I-, 8% IO$_3$- and 10% PVP by mass relative to silicone elastomer (see Example 4).

Figure 4. Recovery of free $I_2$ at varying intervals following submersion of silicone fabricated device in 100 mM sodium citrate, pH 4.0, in a formulation consisting of 2% $I^-$, 8% $IO_3^-$ and 10% PVP by mass relative to silicone elastomer (see Example 4).

Figure 5.  De novo formation of free $I_2$ released from $I-/IO_3-$ encapsulated 1% "high viscosity" alginate hydrogel upon submersion of fabricated device in 100 mM sodium citrate, pH 4.0. Control used same hydrogel composition excluding $I-/IO_3-$ from formulation (see Example 5).

Figure 6. Comparison of kinetic rates of free $I_2$ generation at pH 4.5 versus pH 7.4 using proton driven reaction through production of gluconic acid via GO and HPO oxidative activity on inorganic I- and glucose (see Example 6).

Figure 7. Recovery of $IO_3^-$ (solid lines) and $I^-$ (dashed lines) at varying intervals following submersion of 5 cm length prefarbricated silicone (square symbols) and polyethylene (triangle symbols) cannulae in 100 mM sodium citrate, pH 4.0, after coating each in thin layers of $I^-/IO_3^-$ encapsulated silicone polymers (see Example 7).

MEDICAL DEVICE HAVING ANTI-INFECTIVE AND CONTRACEPTIVE PROPERTIES

CROSS REFERENCE TO RELATED APPLICATIONS

This application claims the benefit under 35 USC 119(e) of copending Provisional Application No. 60/090,014, filed on Jun. 19, 1998, and is a continuation-in-part application of, and claims the benefit under 35 USC 120 of, application Ser. No. 09/179,233, filed on Oct. 26, 1998, and application Ser. No. 09/265,196, filed on Mar. 10, 1999, now abandoned. These applications and other documents referred to elsewhere in the specification of this application are incorporated herein by reference in their entireties.

TECHNICAL FIELD OF THE INVENTION

The present invention relates to the field of medical devices, and more particularly to devices having controlled spermicidal, microbicidal, and virucidal activities.

BACKGROUND OF THE INVENTION

Introduction of medical devices implanted into the body can lead to serious nosocomial infections. Implanted medical devices (e.g., venous and arterial catheters, neurological prostheses, shunts and stents, joint implant prostheses, urinary "Foley" catheters, peritoneal catheters, lead wires to pacemakers, etc.), while sterilized and carefully packaged to guard against introduction of pathogens during implantation, pose a risk during insertion, and subsequently. During insertion bacteria can be picked up from the skin and carried into the insertion site where colonization ensues. In the case of urinary catheters, especially those used long term, there is a significant threat of microbial growth along the exterior surface of the catheter. This can lead to chronic urinary tract infections (CUTI), especially among the elderly. Methods aimed at circumventing this problem have included, for example, the coating of implant devices with antibiotics before insertion, irrigating the implant site with antibiotic, applying various antibiotic ointments or antibiotic impregnated sponges near the exterior opening by which infection most likely occurs, impregnating the polymer base coating the implant device with antibiotics, or treatment of patients systemically with antibiotics. However, despite the foregoing attempts and the overuses of antibiotics involved (with the attendant risks of developing resistant strains of bacteria), there remains a need in the art to mitigate the risk of infection from such devices that are implanted and have external environment exposure.

Long term use or misuse of antibiotics often results in the selection of antibiotic resistant strains. Hence, in general, systemic antibiotic therapy is ill advised and ineffective in warding off CUTI. The secondary side effects of systemic antibiotic treatments can also pose a serious risk to many patients. Furthermore, in many implant sites, the formation of fibrous tissue around the implant site reduces the supply of blood to the implant cavity thereby precluding systemic antibiotic treatment of the critical space between the implant and capsular endothelial wall. In the case of a urinary catheter (e.g., Foley catheter), antibiotics injected as a coating in the urinary canal may be washed out during drainage through leakage of some urine along the urinary tract outside the catheter, or resorbed before they can achieve sufficient levels to effectively kill bacteria growing within localized regions of the urinary tract.

Aside from implants, there are other commonly acquired infections that cause significant suffering and health complications in the general population. Vaginal infections, for example, are a frequent cause of health problems in women. They are a source of distress and discomfort, and can lead, in some instances, to sterility, to tubal ectopic pregnancy, and increased incidences in the transmission of human immunodeficiency virus (HIV). *Chlamydia trachomatis*, a sexually transmitted bacterium, is a serious problem in that it can infect young women of child-bearing age without producing any initial overt symptoms, but causing extensive scaring of the cervix and permanent loss of fertility. Other serious infections acquired during, or prior to pregnancy, but undetected, can result in a multitude of complications to the unborn fetus, or lead to pPROM (preterm premature rupture of membranes before the onset of labor), a major factor contributing to preterm births.

The most common vaginal infections among women are bacterial vaginosis (BV) (sometimes referred to as nonspecific vaginitis or *Gardnerella*-associated vaginitis), trichomoniasis (sometimes referred to as "trich"), and vulvovaginal candidiasis (VVC) (sometimes referred to as candidal vaginitis, monilial infection, or vaginal yeast infection). In infections associated with pPROM, certain women are prone to colonization by group B *Streptococcal* strains that pose a particularly serious threat in terms of premature delivery and life-threatening complications to the fetus.

Microbicidal treatments for vaginal infections include oral prescription medications and over the counter (OTC) topical applications, suppositories and douches. Topical medications are messy to apply, and require daily applications over a period of up to a full week. A difficult problem in the use of OTC medications is that the infection may be misdiagnosed and treated inappropriately, resulting in more complicated problems for the user. Some women, for example, inadvertently treat for yeast infections with OTC medications, applying antifungal agents to bacterial infections (including STDs) which are not responsive to this mode of treatment, and thus fail to obtain timely medical treatment.

These problems underscore the need for better treatment devices and for devices designed for prevention of chronic acquired infections associated with implant insertion into body cavities, and, for example, the treatment of BV and pPROM.

Additionally, there is a need for female-controlled contraceptive methods that are effective against pregnancy and infection. There is widespread recognition of the burden of unplanned pregnancies, and the spread of (sexually transmitted diseases) STDs (including AIDS) in contributing to human suffering worldwide. Although tubal ligations and vasectomies provide effective treatments in eliminating unplanned pregnancies, neither provides adequate protection against the spread of STDs (Armstrong, *Morbidity Mortality Weekly Report* 41:149, 1992). Also, these methods are generally irreversible, rendering them unacceptable to many couples who intend, in the future, to have children. Hormonal methods of birth control (e.g., Norplant®, oral contraceptives, DMPA, vaginal ring), while efficacious in reversibly blocking unwanted pregnancies, offer limited protection against STDs (Cates and Stone, *Family Planning Perspectives* 24:75–84, 1992). Spermicidal agents, chiefly nonoxynol-9 and varying analogues of this detergent, have a number of drawbacks including irritation of the vaginal mucosal tissues, rapid adsorption across mucosal tissues, and nonspecificity in disrupting indiscriminately the lipid bilayers of cells. There is also some evidence that mucosal lesions of the vagina and cervix, induced by frequent use of nonoxynol-9, facilitate the transmission and spread of the HIV virus. In addition, the use of detergents, such as nonoxynol-9, in combination with diaphragms, cervical caps and condoms is problematic in that they can weaken and degrade the polymers used in the fabrication of these barrier devices. Moreover, diaphragms and cervical caps offer only limited protection against STDs, and have failure rates in terms of unplanned pregnancies in the range of 12 to 24% (Speroff and Darney eds. *A Clinical Guide for Contraception*, 2nd edition. Williams & Wilkins, Baltimore, Md. pp. 229–262, 1996; and Mauk et al. *Contraception* 53:329–335, 1996).

Of all the current birth control methods available, the male condom is the only device that has FDA labeling indicating it is effective in reducing the transmission of STDs. However, the male condom fails to address the need for a female-controlled birth control method that further limits exposure to both STDs and unplanned pregnancies.

An important aspect of an effective contraceptive is that it does not require frequent attention, or particular skills in its proper use. Indeed, methods requiring daily attention prior to intercourse have practical failure rates two-fold higher (or higher in some instances) than predicted under ideal use. As an example, the male condom has an expected failure rate, in terms of unplanned pregnancies per year, in the range of 3%, but a practical failure rate in the range of 14%. This failure rate compares with the "natural" withdrawal rate that is in the range of 19%. Of those methods requiring the least attention (e.g., sterilization, hormonal methods, and IUD), while effective, they are inadequate in providing full protection against the spread of STDs. Further, many women dislike long term use of hormonal methods of birth, and they have an aversion to the use of IUD's, in part, because of evidence that IUD's can cause pelvic inflammatory disease and ectopic pregnancies (e.g., the "Dalkon Shield" experience). Thus, there is a need in the art for improved birth control methods that are more effective and convenient to use, which are also safe, and which block the transmission of infectious diseases.

Iodine as an Anti-Infective Agent

In the treatment of infections, elemental iodine is of significance as a prospective anti-infective agent. Iodine has intrinsic chemical properties which could be exploited in conferring to implant devices novel and efficacious anti-infective activities in the treatment, and prevention, of opportunistic infections. Iodine has been used for over 150 years in various formulations as a sterilizing agent.

Iodine exists in several oxidation states including its fully reduced iodide ($I^-$) state, its diatomic elemental state ($I_2$) (hereafter "elemental iodine"), and in several higher oxidation states in combination with oxygen (e.g., hypoiodate ($IO^-$), iodate ($IO_3^-$) and periodate ($IO_4^-$)). In aqueous solutions iodide forms an equilibrium complex with elemental iodine, yielding soluble tri-iodide ($I_3^-$) which exhibits neither significant microbicidal nor virucidal activity. On the other hand, trace quantities (e.g., a few ppm) of elemental iodine are sufficient to cross the lipid bilayer of cells, and sufficient to kill micro-organisms through oxidative reactions within their lipid bilayer. Extensive studies have also shown that microorganisms are incapable of developing resistance against elemental iodine because of its ability to oxidize and intercalate into multiple sites within microbes.

Problems in the Delivery and Formulation of Iodine as an Anti-Infective Agent

Early attempts at improving formulations in extending the shelf life of iodine solutions designed for anti-infective treatments used alcohol as a carrier in trapping iodine in solution. The formulations, referred to as tincture of iodine, proved unsatisfactory because the high alcohol content required to retain elemental iodine in solution proved, itself, inflammatory. A more satisfactory method of trapping elemental iodine in solution evolved with the development of iodophors of iodine (e.g. complexed forms of elemental iodine in solution using specific organic binding agents). Among the better known iodophors formulated to create a potent anti-infective iodine solution was povidone-iodine, also known as Betadine®, a water soluble polyvinylpyrrolidone organic polymer mixed with iodide and elemental iodine. In this formulation elemental iodine binds to the hydrophobic polyvinylpyrrolidone backbone as well as to the cationic pyrrole nitrogen in the form of a tri-iodide complex. The rationale to this formulation was that elemental iodine would be available through equilibrium with loosely bound (e.g., "available") iodine complexed to polyvinylpyrrolidone.

Elemental iodine (i.e., free $I_2$) is actually only a very small fraction of the total iodine in commercial anti-infective formulations, such as povidone-iodine. 10% povidone-iodine, for example, is formulated at ~1% total "available" iodine (e.g., 10,000 ppm), whereas its elemental iodine concentration varies from ~0.8 to 1.2 ppm (*Ellenhorn's Medical Toxicology: Diagnosis and Treatment of Human Poisoning*, $2^{nd}$ edition). While this level of elemental iodine is marginally effective as a microbicide, it comes at a cost. LeVeen et al. (*Surgery, Gynecology & Obstetrics* 176: 183–190, 1993) have pointed out several deficiencies in povidone-iodine formulations including the tradeoff of a very low elemental iodine level (e.g., approx. 1 ppm). Low elemental iodine makes povidone-iodine relatively ineffective as an anti-infective agent except against extremely sensitive bacteria. Povidone-iodine solutions also fail to treat severe vaginitis, and cause complications associated with formation of granulomas in wounds, as a result of residual polyvinylpyrrolidone in formulations applied to the wound site.

Additionally, elemental iodine is not available in sufficient concentrations in commercial formulations to use as a spermicidal agent. WHO (the World Health Organization) defines standards for spermicide testing and requires that a spermicide completely immobilize all sperm with which it comes into contact within 20 seconds. These standards reflect the fact that sperm spend a very short time (seconds) within the vaginal vault following ejaculation into the vagina before passing through the cervical os. Thus, an effective spermicide must be capable of rapidly immobilizing sperm before they can pass through the cervical os and into the uterus. These WHO criteria are an important standard for testing contraceptive devices. Others have sought to use iodine formulations in birth control applications either in the form of povidone-iodine, in complexes with polyurethane, or in combination with nonoxynol-9, but have failed to demonstrate adequate spermicidal activity in accordance with the standards defined by WHO. For example, povidone-iodine in the range of 1% and higher total iodine was found to require upwards of 10 minutes exposure to semen samples before the sperm lost motility, whereas 0.1% and lower concentrations of povidone-iodine failed, or even stimulated, sperm motility (Pfannschmidt et al. U.S. Pat. No. 5,545,401). Several patents have disclosed the use of povidone-iodine (or iodine complexed with polyurethane) as a spermicide or in combination with ionic or nonionic detergents (see, for example, U.S. Pat. Nos. 5,545,401; 5,577,514; 4,922,928; 5,156,164; and 5,466,463). However, there is no evidence that iodine formulations of the type disclosed, in any fashion, confer enough spermicidal activity sufficient to put these formulations into practice according to WHO criteria.

Other characteristics of povidone-iodine also make it impractical to use as an intravaginal anti-infective agent, even in combination with other spermicidal agents. For example, the intense brownish-red coloration of this solution makes it unattractive esthetically and unacceptable to users. In addition, the use of povidone-iodine formulations, in combination with such spermicidal detergents as nonoxynol-9, is problematic in that iodine causes the detergent moiety to precipitate out of solution. In the presence of quaternary ammonium detergents, both iodine and triiodide form insoluble complexes in binding to the quaternary ammonium moiety that causes the detergent to precipitate out of solution. Hence, combining iodine with the common spermicidal detergent, nonoxynol-9, related polyunsaturated detergent polymers, or cationic quaternary ammonium detergents produces products that lose their spermicidal properties through chemical modification and precipitation from solution.

An attempt to circumvent problems associated with formulations containing povidone-iodine in recognition of the fact that elemental iodine is the active agent conferring anti-infective activity was made by Shikani and Domb (*J. Amer. College of Surgeons* 183:195–200, 1996; U.S. Pat. No. 5,762,638). The authors coated plastic implant devices with layers of elemental iodine dissolved in a polymer base in such a manner so as to cause adherence of the iodine-polymer on the surface of the implant device. This approach has several limitations. It is costly and, as pointed out by Shikani and Domb, it is limited to polymeric implant devices which can tolerate solvents used in dissolving the iodine-loaded polymer coating, and which are chemically compatible in forming a strong and intact bond between the iodine impregnated polymer coating and implant polymer substratum. Polymers which swell in biological fluids (a common phenomenon) also cannot be used in this technology because swelling leads to a rupture of the coated outer layer, and thereafter a failure of the controlled release rates of the impregnated iodine to the surrounding sites requiring anti-infective treatment.

Within the body, a variety of naturally occurring oxidants are produced which function as anti-infective agents. The major source of oxidizing activity accounting for development of anti-infective activities in the body can be traced to the initial formation of superoxide and hydrogen peroxide through a variety of oxidizing pathways. These initial oxidants are known to catalyze in the presence of halides, trace metals, thiocyanate (a natural constituent of particular abundance in saliva believed to confer to the mouth certain unique antimicrobial properties when converted to hypothiocyanite), and amines, a cascading armada of anti-infective products including (in addition to superoxide and hydrogen peroxide) hydroxyl radicals, hypohalites (e.g., hypochlorite, hypobromite), haloamines (e.g., chloramine), hypothiocyanite, and nitric oxide, all of which have been shown to exhibit varying degrees of antimicrobial activity (Klebanoff, S. J. and Clark, R. A. (1978) in The Neutrophil: Function and Clinical Disorders, North-Holland Publishing Company, Amsterdam; Halliwell, B. and Gutteridge, J. M. (1990) Role of Free Radicals and Catalytic Metal Ions in Human Disease: An Overview. *Meth. Enzymol.* 186, 1–85; Southorn, P. A. and Powis, G. (1988) Free Radicals in Medicine. I. Chemical Nature of Biological Reactions. May Clinic Proc. 63, 390–498; Pryor, W. A., ed., in Free Radicals in Biology, Academic Press, New York, 1976–1984), Vol. 1–6; Klebanoff, S. J. (1991) in Peroxidases in Chemistry and Biology (Everse, J., Everse, K. E. and Grisham, M. B., eds.), pp. 1–35, CRC Press, Boca Raton; Tenovuo, J. (1997) Salivary Parameters of Relevance for Assessing Caries Activity in Individuals and Populations. *Community Dent. Oral Epidemiol.* 25: 82–6; Carlsson, J., Edlund, M. B. and Hanstrom, L. (1984) Bactericidal and Cytotoxic Effects of Hypthiocyanite-Hydrogen Peroxide Mixtures. Infection & Immunity 44: 581–6.). Elemental iodine, while also easily formed in the presence of these naturally occurring oxidants, ordinarily is not formed as an anti-infective in the body defenses against microorganisms because the concentration of iodide in tissues and body fluids, with the exception of the thyroid gland, are too low relative to chloride, the most abundant halide found in body tissues and fluids. Thus hypochlorite and chloramines are produced within the body in far greater abundance than hypoiodite and iodamines under physiological conditions.

Accordingly, it can be appreciated from the above observations that there is a need for fabricating medical devices such as cannulas, catheters and the like, and other types of implants with microbicidal, virucidal, or spermicidal activity, aimed at treating ongoing infections, preventing infections that gain access through the implanted devices, or providing contraceptive and anti-infective properties, with improved performance over current antibiotic, iodophor treatments, or contraceptive systems.

SUMMARY OF THE INVENTION

The present invention provides a medical device comprising a polymeric matrix containing an oxidant producing component within the matrix which is stable at least until the device is contacted by water. The term stable as used herein should be understood to mean that the device will not produce an oxidant at least until the device is contacted by water and the oxidant producing component is solvated. The water may be provided by exposing the device to body fluids during use, or by wetting the device just prior to use. The invention provides an anti-infective medical device due to the production of an anti-infective oxidant, which in one embodiment, provides contraceptive spermicidal activity. The term medical device should be understood to include a variety of devices including catheters, dressings, implants, prostheses, contraceptive barriers, and gloves.

The anti-infective medical device of the invention produces an oxidant having anti-infective properties due to its oxidative activity. The anti-infective oxidant produced by the oxidant producing component has microbicidal and virucidal activity, and in one embodiment, spermicidal activity. Suitable anti-infective oxidants include elemental iodine, hydrogen peroxide, superoxide, nitric oxide, hydroxy radical, hypohalites, haloamines, thiocyanogen, and hypothiocyanite. The anti-infective oxidants are produced by the oxidation, reduction, or hydrolysis of the oxidant producing component.

In the case of elemental iodine, the oxidant producing component is an iodine-containing salt which is oxidized or reduced, to produce elemental iodine. A source of protons is generally required to drive the oxidation or reduction of iodine-containing salt to elemental iodine. Iodine-containing salts suitable for use in the invention include iodides, which oxidize to elemental iodine, and iodates, which reduce to elemental iodine. Suitable iodides include any of the iodides of alkali and alkaline earth metals, such as sodium iodide, potassium iodide, calcium iodide, and barium iodide. Suitable iodates include iodates of alkali metals such as sodium iodate, potassium iodate, and iodine pentoxide. In the case of iodates, the iodate may act as both a source of iodide, and an oxidizing agent which oxidizes iodide to elemental iodine.

In the case of hydrogen peroxide as the anti-infective oxidant, a variety of suitable oxidant producing compounds may be used including peroxy acid precursors and hydrogen peroxide addition compounds, such as percarbamides, perborates, percarbonates, persulfates and peroxides, which hydrolyse or solvate to produce hydrogen peroxide. Alternatively, substrate oxidoreducatases may be used in which hydrogen peroxide is formed as either a direct or an indirect product of the catalytic reduction of molecular oxygen. In the case of hypohalite as the anti-infective oxidant, the oxidant producing component comprises a halide-containing compound oxidized by an oxidizing agent to produce the hypohalite. Similarly, a thiocyanogen or hypothiocyanite anti-infective oxidant can be produced by the oxidation of a thiocyanate.

A variety of suitable oxidizing agents may be used to oxidize the oxidant producing component, including iodine oxide salts, peracids, and substrate oxidoreducatases. Suitable iodine oxide salts include alkali or alkaline earth metal iodates such as potassium iodate, sodium iodate or calcium iodates, and iodine pentoxide. Suitable peracids include perborates and organic peroxyacids.

A variety of suitable reducing agents may be used to reduce the oxidant producing component. For example, where the oxidant producing component is an iodate, any iodate oxidizable substrate such as ascorbate, thiols, and organic aldehydes may provide the reducing equivalents to reduce iodate to elemental iodine. In the case of intravaginal use, these reducing agents may be present in the intracorporeal environment in which the medical device is used.

A variety of suitable proton producing agents may be used including an anhydride which upon exposure to water spontaneously hydrolyzes to an acidic product, or an enzyme acting on a substrate which catalyzes formation of an acid product. In a presently preferred embodiment, the proton producing agent is selected from the group consisting of iodine pentoxide, an organic or inorganic acid, and enzyme oxidase, and an anhydride such as succinic anhydride, maleic anhydride, succinyl maleic anhydride and acetic anhydride.

In one aspect of the invention, the anti-infective medical device comprises a polymeric matrix which contains all the oxidant precursor component(s) necessary to produce the anti-infective oxidant, except for water to solvate the component(s), so that the oxidant producing compound is stable until the device is contacted by water. In accordance with the invention, the oxidant precursor component(s) may consist of one component, namely an oxidant producing component which merely requires hydrolysis or solvation to produce the oxidant. Alternatively, the oxidant precursor component(s) contained in the polymeric matrix may include an oxidant producing component and one or more of an oxidizing agent, a reducing agent, and a proton source.

In another aspect of the invention, the anti-infective medical device comprises a polymeric matrix which does not contain one or more reactants required for reacting with the oxidant producing component to form the oxidant. For example, an oxidizing or reducing agent, or a reactant which forms the oxidizing or reducing agent, or a proton source may be absent from the polymeric matrix, so that the oxidant producing component is stable until contacted by water and by the oxidizing or reducing agent, and/or proton source. The missing reactants may be provided by the body fluid which contacts the device during use. For example, hydrogen peroxide as an oxidizing agent may be produced by a substrate oxidase enzyme in which one or both of the substrate and the enzyme is provided by the body fluid. Thus, device stability is achieved by providing a device which lacks one or more reactants (i.e., water, oxidizing or reducing agents, and protons) required to produce the anti-infective oxidant. The medical device of the invention may provide sustained release of the oxidant, so that the anti-infective or spermicidal activity of the medical device is provided over a length of time depending on a variety of factors including the concentration and nature of the oxidant precursor component(s), and the configuration of the polymeric component containing the oxidant precursor component(s).

A variety of suitable polymers may be used as the polymeric matrix including thermoplastic polymers, thermosetting polymers, and hydrogels. Polymeric materials typically used in medical devices which are suitable for use in the invention include silicone, polyolefins, polyamides, polyesters, polyethers, polyurethanes, polycarbonates, polyacrylates, and fluoropolymers. Suitable hydrogels include polyacrylates, celluloses, and starch. Particles of the oxidant producing component, and optionally one or more of a reducing agent, oxidizing agent, and proton source, are typically added to the polymeric material (or to elastomers of a two-component formulation), which is then processed by a variety of suitable methods such as molding or extruding into the medical device. In the case of a two-component elastomer formulation such as a polymethylvinyl siloxane (Part A) and the second catalytic formulation comprising a platinum catalyst and methyl hydryl siloxane (Part B), particles of the oxidant producing component, oxidizing agent and proton sources may be added separately to either Part A or B of the two-component elastomers in forming master batches which upon mixing together result in cured polymers containing the anti-infective and spermicidal formulation entrapped within the cured polymer matrix. Alternatively, in thermomelt polymers, the solid particle formulations are typically mixed into the polymer base at, or slightly above, its melting point where the polymer takes on a liquid state, and then entrapped as a dispersion in the polymer matrix as the polymer is then cooled below its melting point. The oxidant producing component may be contained throughout the polymeric material of the anti-infective medical device. Alternatively, a layer of the polymeric material containing the oxidant producing component may be provided as a coating on a surface of the medical device. For example, a catheter having a shaft and a lumen therein may have a the oxidant producing component throughout the shaft, or alternatively, may have a layer of polymeric material containing the oxidant producing component on at least one of an inner surface and an outer surface of the catheter shaft. The configuration used will depend on a variety of factors including the desired concentration of oxidant, the polymeric material, and application. For example, a layer of polymeric material containing the oxidant producing component may be applied as a coating to a medical device formed of a nonpolymeric material or a polymeric material which has characteristics or processing conditions which make adding the oxidant producing component to the polymeric material undesirable, or impractical.

In a first embodiment, the present invention provides an implantable device having anti-infective activity, comprising a solid hydrophobic polymeric material suitable for medical implantation containing therein and further comprising a dry oxidant-generating formulation, which in a presently preferred embodiment is an iodine-generating formulation, and wherein the dry iodine-generating component is a dry mixture of an iodine salt selected from the group consisting of anhydrous potassium iodide, anhydrous sodium iodide, and combinations thereof, and an oxidizing agent, wherein the oxidizing agent is selected from the group consisting of anhydrous alkali iodine oxide salts, inorganic or organic peracids, a $H_2O_2$ generating oxidase enzyme, and combinations thereof. Preferably, the solid polymeric material is a silicone elastomer.

Preferably, the concentration of anhydrous potassium iodide, anhydrous sodium iodide, or both is from about 0.01% to about 16% (by weight) of the solid polymeric material. Preferably, the anhydrous alkali iodine oxide salts are selected from the group consisting of anhydrous sodium iodate, iodine pentoxide, and combinations thereof. Preferably, inorganic or organic peracids are selected from the group consisting of perborates, organoperoxy acids, and combinations thereof. Most preferably the inorganic or organic peracids, if the only oxidizing agent present in the formulation, are provided at a concentration of from about 0.01% to about 16% (by weight) of the solid polymeric material. Preferably, the $H_2O_2$ generating oxidase enzyme is selected from the group consisting glucose oxidase, diamine oxidase, and combinations thereof. The term glucose oxidase as used herein should be understood to mean D-glucose:oxygen 1-oxidoreductase; EC 1.1.3.4, and the term diamine oxidase as used herein should be understood to mean amine:oxygen oxidoreductase[deaminating] [pyridoxal-containing] ; EC 1.4.3.6. Most preferably the $H_2O_2$ generating oxidase enzyme further comprises a peroxidase enzyme. The term peroxidase enzyme should be understood to mean donor:hydrogen-peroxide oxidoreductase; EC 1.11.1.7. Preferably, the $H_2O_2$ generating oxidase enzyme, if the only oxidizing agent present in the formulation, is present at a concentration of from about 0.01% to about 2.5% (by weight) of the solid polymeric material. Most preferably, the glucose oxidase (D-glucose:oxygen 1-oxidoreductase; EC 1.1.3.4) is present at a concentration of at least 0.01% by weight of the solid polymeric material, wherein the specific activity of glucose oxidase is in the range of 2,000 to 200,000 IU per gram of solid (i.e., per gram of glucose oxidase) and a peroxidase (donor:hydrogen-peroxide oxidoreductase; EC 1.11.1.7) is present at a concentration of at least 0.01% by weight of the solid polymeric material wherein the specific activity of peroxidase is in the range of 250,000 to 330,000 IU per gram of solid, with the proviso that the sum concentration of a combination of oxidase and peroxidase enzymes is within the range of from about 0.01% by weight to about 2.5% by weight of the solid polymeric material. Most preferably, the diamine oxidase (amine:oxygen oxidoreductase[deaminating] [pyridoxal-containing]; EC 1.4.3.6) is present in the formulation at a concentration of at least 0.01% by weight of the solid polymeric material, wherein the specific activity of diamine oxidase is in the range of 50 to 800 IU per gram of solid, and a peroxidase (donor:hydrogen-peroxide oxidoreductase; EC 1.11.1.7) is present at a concentration of at least 0.01% by weight of the solid polymeric material, wherein the specific activity of peroxidase (donor:hydrogen-peroxide oxidoreductase; EC 1.11.1.7) is in the range of 250,000 to 330,000 IU per gram of solid, with the proviso that the concentration of the $H_2O_2$ generating oxidase enzymes is within the range of from about 0.01% to about 2.5% by weight of the solid polymeric material. Preferably, the formulation further comprises a desiccant to stabilize the iodine salts from absorbing moisture from the atmosphere and prematurely solvating and forming iodine. Preferably a desiccant is selected from the group consisting of a dry powder mixture of from about 1% to about 10% (by weight) polyvinylpyrrolidone, $CaCl_2$ and combinations thereof.

In a second embodiment, the present invention further provides a hydrogel anti-infective or contraceptive device, comprising a hydrogel agent and an iodine-generating formulation, wherein the iodine generating formulation comprises an iodide and an oxidizing means, wherein the iodide is selected from the group consisting of potassium iodide, sodium iodide, and combinations thereof, wherein the oxidizing means is present in an amount sufficient to release iodine from the iodide.

Preferably, the oxidizing means is selected from the group consisting of alkali iodine oxide salts, peracids, $H_2O_2$-generating enzyme oxidases, and combinations thereof. Most preferably, the alkali iodine oxide salts are sodium iodate, or iodine pentoxide or both. Most preferably, the peracids are perborates, peracetates, or both. Most preferably, the $H_2O_2$ generating enzyme oxidases are selected from the group consisting of glucose oxidase (D-glucose:oxygen 1-oxidoreductase; EC 1.1.3.4) or diamine oxidase (amine:oxygen oxidoreductase[deaminating] [pyridoxal-containing]; EC 1.4.3.6) and combinations thereof. Preferably, the $H_2O_2$ generating enzyme oxidases optionally includes a peroxidase enzyme. Preferably, the peroxidase enzyme is donor:hydrogen-peroxide oxidoreductase; EC 1.11.1.7.

Preferably, the hydrogel agent is a polycarboxylic or polyhydroxyl complex polymer selected from the group consisting of linear polyacrylates, cross-linked polyacrylates, hydroxyalkyl celluloses, polycarboxyalkyl celluloses, water soluble celluloses, polyethylene alcohols, vinyl alcohols, chitosan polymers, salts of alginic acid, and combinations thereof. Preferably, the hydrogel agent is made up to not less than about 0.2% (by weight) in water, and not more than about 5% by weight in water. Most preferably, the hydrogel agent is about 2% by weight of the formulation. Preferably, the pH of the formulations is from about pH 3.0 to about pH 6.5. Most preferably, the pH is about 4.0.

Preferably, the concentration of iodide in the hydrogel device formulation is from about 0.1 mM to about 200 mM. Preferably, the hydrogel device formulation oxidizing means is present in the formulation at a concentration from about 0.1 mM to about 200 mM when the oxidizing means is an alkali oxide of iodine or a peracid. Preferably, the hydrogel device formulation oxidizing means is present in the formulation at a concentration from about 2 μg/ml to about 500 μg/ml when the oxidizing means is a $H_2O_2$ generating enzyme oxidase. Preferably, the glucose oxidase (D-glucose:oxygen 1-oxidoreductase; EC 1.1.3.4) made up at a specific activity is in the range of 2,000 to 200,000 IU per gram of solid, or diamine oxidase (amine:oxygen oxidoreductase[deaminating] [pyridoxal-containing]; EC 1.4.3.6) is made up at a specific activity is in the range of 50 to 800 IU per gram of solid. Preferably, the peroxidase (donor:hydrogen-peroxide oxidoreductase; EC 1.11.1.7) enzyme is present at a concentration of from about 2 μg/ml to about 500 μg/ml when its specific activity is in the range of 250,000 to 330,000 IU per gram of solid.

The present invention further provides a hydrogel anti-infective and contraceptive device, comprising a hydrogel member having a circular shape suitable for vaginal insertion and retention in the cervical region and formed by a process comprising:
(a) admixing a hydrogel-forming formulation with an aqueous iodine-generating formulation, wherein the iodine generating formulation comprises an iodide and an oxidizing means, and wherein the hydrogel-forming formulation comprises a hydrogel agent, wherein the iodide is selected from the group consisting of potassium iodide, sodium iodide, and combinations thereof, wherein the oxidizing means is present in an amount sufficient to release iodine from the iodide, and wherein the hydrogel agent is selected from the group consisting of linear polyacrylates or cross-linked polyacrylates, hydroxyalkyl celluloses, polycarboxyalkyl celluloses, water soluble cellulose, polyethylene or vinyl alcohols, chitosan polymers, salts of alginic acid, or combination thereof, to form a hydrogel device formulation; and
(b) pouring the hydrogel device formulation into a mold to form a semi-solid in a shape of the mold, wherein the mold forms a ring-shape or a disc-shape.

The hydrogel-forming formulation may be provided with a viscosity augmentor when desired, as for example in the the case of a vaginal device for contraception and infections. Most preferably, the viscosity augmentor is a polycarboxylic or polyhydroxyl complex polymer selected from the group consisting of linear polyacrylates, cross-linked polyacrylates, hydroxyalkyl celluloses, polycarboxyalkyl celluloses, water soluble celluloses, polyethylene alcohols, vinyl alcohols, chitosan polymers, salts of alginic acid, and combinations thereof. Preferably, the viscosity augmentor is made up to not less than about 0.2% (by weight) in water, and not more than about 5% by weight in water. Most preferably, the viscosity augmentor is about 2% by weight of the aqueous formulation. Preferably, the pH of the hydrogel-forming device formulation is from about pH 3.0 to about pH 6.5. Most preferably, the pH is about 4.0.

Preferably, the anti-infective device that is either the hydrophobic polymer embodiment or the hydrogel embodiment is shaped to either conform to a body cavity, a specific implant design, or a thin sheet of not less than 0.1 mm in thickness or greater than 10 mm in thickness. Most preferably, a vaginal implant shape is formed into a circular shape suitable for vaginal insertion and retention in the cervical region. Suitable device circular shapes are ring, concave disc, and tampon. In the ring configuration designed to fit near the formix between the vaginal wall and cervix, the device should have an outer diameter of from about 3.0 cm to about 7.0 cm. Most preferably, the outer diameter is from about 5.6 cm to about 6.0 cm. The inner, hollow core of the ring diameter should range from about 2.0 to about 6.0 cm, allowing for a ring of from about 0.5 to 1.5 cm in thickness, most preferably exhibiting a hollow core diameter of from about 4.6 to 5 cm, and a ring of from about 0.8 to about 1.2 cm in thickness.

In a third embodiment, the present invention further provides a bilayer hydrogel anti-infective device, comprising a first bilayer member comprising a hydrogel agent and a first component of an iodine-generating formulation and a second bilayer member comprising a hydrogel agent and a second component of an iodine-generating formulation, wherein the first component of the iodine generating formulation comprises an iodide and the second component of the iodine-generating formulation comprises an oxidizing means, wherein the iodide is selected from the group consisting of potassium iodide, sodium iodide, and combinations thereof, wherein the oxidizing means is present in an amount sufficient to release iodine from the iodide, and wherein the hydrogel agent is selected from the group consisting of linear polyacrylates or cross-linked polyacrylates, hydroxyalkyl celluloses, polycarboxyalkyl celluloses, water soluble cellulose, polyethylene or vinyl alcohols, chitosan polymers, salts of alginic acid, or combination thereof.

Preferably, the oxidizing means is selected from the group consisting of alkali iodine oxide salts, peracids, $H_2O_2$-generating enzyme oxidases, and combinations thereof. Most preferably, the alkali iodine oxide salts are potassium or sodium iodate, iodine pentoxide or both. Most preferably, the peracids are perborates, peracetates, or both. Most preferably, the $H_2O_2$ generating enzyme oxidases are selected from the group consisting of glucose oxidase (D-glucose: oxygen 1-oxidoreductase; EC 1.1.3.4) or diamine oxidase (amine:oxygen oxidoreductase[deaminating] [pyridoxal-containing]; EC 1.4.3.6) and combinations thereof. Preferably, the $H_2O_2$ generating enzyme oxidases optionally includes a peroxidase enzyme. Preferably, the peroxidase enzyme is donor:hydrogen-peroxide oxidoreductase; EC 1.11.1.7.

Preferably, the hydrogel agent is a polycarboxylic or polyhydroxyl complex polymer selected from the group consisting of linear polyacrylates, cross-linked polyacrylates, hydroxyalkyl celluloses, polycarboxyalkyl celluloses, water soluble celluloses, polyethylene alcohols, vinyl alcohols, chitosan polymers, salts of alginic acid, and combinations thereof. Preferably, the hydrogel agent is made up to not less than about 0.2% (by weight) in water, and not more than about 5% by weight in water. Most preferably, the hydrogel agent is about 2% by weight of the formulation of either the first or the second component. Preferably, the pH of the formulations is from about pH 3.0 to about pH 6.5. Most preferably, the pH is about 4.0.

Preferably, the concentration of iodide in the bilayer hydrogel device formulation is from about 0.1 mM to about 200 mM. Preferably, the bilayer hydrogel device formulation oxidizing means second component is present at a concentration from about 0.1 mM to about 200 mM when the oxidizing means is an alkali oxide of iodine or a peracid. Preferably, the hydrogel device formulation oxidizing means second component is present at a concentration from about 2 μg/ml to about 500 μg/ml when the oxidizing means is a $H_2O_2$ generating enzyme oxidase. Preferably, the glucose oxidase (D-glucose:oxygen 1-oxidoreductase; EC 1.1.3.4) made up at a specific activity is in the range of 2,000 to 200,000 IU per gram of solid, or diamine oxidase (amine: oxygen oxidoreductase[deaminating] [pyridoxal-containing]; EC 1.4.3.6) is made up at a specific activity is in the range of 50 to 800 IU per gram of solid. Preferably, the peroxidase (donor:hydrogen-peroxide oxidoreductase; EC 1.11.1.7) enzyme is present at a concentration of from about 2 μg/ml to about 500 μg/ml when its specific activity is in the range of 250,000 to 330,000 IU per gram of solid.

In a fourth embodiment, the present invention further provides a coated implantable device having anti-infective activity, comprising an implantable medical device formed of a polymeric material having an anti-infective coating thereon, wherein the anti-infective coating comprises a solid hydrophobic polymeric material suitable for medical implantation containing therein and further comprising a dry iodine-generating formulation, and wherein the dry iodine-generating component is a dry mixture of an iodine salt selected from the group consisting of anhydrous potassium iodide, anhydrous sodium iodide, and combinations thereof, and an oxidizing agent, wherein the oxidizing agent is selected from the group consisting of anhydrous alkali iodine oxide salts, inorganic or organic peracids, a $H_2O_2$ generating oxidase enzyme, and combinations thereof. Preferably, the solid polymeric material is a silicone elastomer.

Preferably, the concentration of anhydrous potassium iodide, anhydrous sodium iodide, or both is from about 0.01% to about 16% (by weight) of the anti-infective coating. Preferably, the anhydrous alkali iodine salts are selected from the group consisting of anhydrous, sodium iodate, iodine pentoxide, and combinations thereof. Preferably, inorganic or organic peracids are selected from the group consisting of perborates, organoperoxy acids, and combinations thereof. Most preferably the inorganic or organic peracids, if the only oxidizing agent present in the formulation, are provided at a concentration of from about 0.01% to about 16% (by weight) of the anti-infective coating material. Preferably, the $H_2O_2$ generating oxidase enzyme is selected from the group consisting of glucose oxidase (D-glucose:oxygen 1-oxidoreductase; EC 1.1.3.4), diamine oxidase (amine:oxygen oxidoreductase[deaminating] [pyridoxal-containing]; EC 1.4.3.6), and combinations thereof. Most preferably the $H_2O_2$ generating oxidase enzyme further comprises a peroxidase (donor:hydrogen-peroxide oxidoreductase; EC 1.11.1.7) enzyme. Preferably, the $H_2O_2$ generating oxidase enzyme, if the only oxidizing agent present in the formulation, is present at a concentration of from about 0.01% to about 2.5% (by weight) of the anti-infective coating material. Most preferably, the glucose oxidase (D-glucose:oxygen 1oxidoreductase; EC 1.1.3.4) is present at a concentration of at least 0.01% by weight of the anti-infective coating material, wherein the specific activity of glucose oxidase is in the range of 2,000 to 200,000 IU per gram of solid and a peroxidase (donor:hydrogen-peroxide oxidoreductase; EC 1.11.1.7) is present at a concentration of at least 0.01% by weight of the solid polymeric material wherein the specific activity of peroxidase is in the range of 250,000 to 330,000 IU per gram of solid, with the proviso that the sum concentration of a combination of oxidase and peroxidase enzymes is within the range of from about 0.01% by weight to about 2.5% by weight of the anti-infective coating material. Most preferably, the diamine oxidase (amine:oxygen oxidoreductase[deaminating] [pyridoxal-containing]; EC 1.4.3.6) is present at a concentration of at least 0.01% by weight of the anti-infective coating material, wherein the specific activity of diamine oxidase is in the range of 50 to 800 IU per gram of solid, and a peroxidase (donor:hydrogen-peroxide oxidoreductase; EC 1.11.1.7) is present at a concentration of at least 0.01% by weight of the anti-infective coating material, wherein the specific activity of peroxidase is in the range of 250,000 to 330,000 IU per gram of solid, with the proviso that the concentration of the $H_2O_2$ generating oxidase enzymes is within the range of from about 0.01% to about 2.5% by weight of the anti-infective coating material. Preferably, the anti-infective coating further comprises a desiccant to stabilize the iodine salts from absorbing moisture from the atmosphere and prematurely solvating and forming free iodine. Preferably the desiccant is selected from the group consisting of a dry powder mixture of from about 1% to about 10% (by weight) polyvinylpyrrolidone, $CaCl_2$ and combinations thereof.

The present invention provides for adding anti-infective properties to a solid implantable device, comprising adding a formulation to the device wherein the formulation comprises iodide, a means for releasing protons, and an oxidant. Preferably, the means for releasing protons is accomplished by hydrolysis of anhydrides or through an enzymatic reaction. Most preferably, the enzymatic reaction uses $H_2O_2$ generating enzymatic oxidation of iodide, wherein the proton sources are supplied by a body fluid exposed to the device, or by wetting the device. The mechanism uses protons generated by the device to chemically convert iodide into elemental iodine, whereas the absence of water or body fluid exposure leaves the device in a dormant state.

In a fifth embodiment, the present invention provides a device for vaginal insertion that provides intra-vaginal generation of anti-infective and spermicidal concentrations of iodine, which in one aspect of the invention involves a mechanical-release anti-infective and contraceptive device, comprising:

(a) a silicone walled tubing having walls defining a reservoir chamber, wherein the walls further comprise a plurality of self-sealing holes extending through the walls and communicating with the reservoir chamber; and (b) an aqueous formulation within the reservoir chamber, wherein the aqueous formulation comprises iodide and an oxidizing means, wherein the iodide is selected from the group consisting of potassium iodide, sodium iodide, and combinations thereof, and wherein the oxidizing means is present in an amount sufficient to release iodine from the iodide upon expulsion of the fluid within the chamber to the external medium and subsequent mixing of the expelled fluid with protons, or substrate sources, present in the latter body fluid, and required for formation of elemental iodine. Alternatively, the substrates, proton source, iodide and oxidizing means may be formulated as a dry mixture to which water is added as a solvating agent immediately before use, and which then serves to solvate and initiate formation of anti-infective and spermicidal iodine. The dry mixture may be within the reservoir chamber, or may be separately combined with water and added to the reservoir chamber just prior to use.

Preferably, the oxidizing means is selected from the group consisting of alkali iodine oxide salts, peracids, $H_2O_2$-generating enzyme oxidases, and combinations thereof. Most preferably, the alkali iodine oxide salts are sodium iodate, or iodine pentoxide or both. Most preferably, the peracids are perborates, peracetates, or both. Most preferably, the $H_2O_2$ generating enzyme oxidases are selected from the group consisting of glucose oxidase (D-glucose: oxygen 1-oxidoreductase; EC 1.1.3.4) or diamine oxidase (amine:oxygen oxidoreductase[deaminating] [pyridoxal-containing]; EC 1.4.3.6) and combinations thereof. Preferably, the $H_2O_2$ generating enzyme oxidases optionally includes a peroxidase enzyme. Preferably, the peroxidase enzyme is donor:hydrogen-peroxide oxidoreductase; EC 1.11.1.7.

Preferably, the aqueous formulation further comprises a viscosity augmentor. Most preferably, the viscosity augmentor is a polycarboxylic or polyhydroxyl complex polymer selected from the group consisting of linear polyacrylates, cross-linked polyacrylates, hydroxyalkyl celluloses, polycarboxyalkyl celluloses, water soluble celluloses, polyethylene alcohols, vinyl alcohols, chitosan polymers, salts of alginic acid, and combinations thereof. Preferably, the viscosity augmentor is made up to not less than about 0.2% (by weight) in water, and not more than about 5% by weight in water. Most preferably, the viscosity augmentor is about 2% by weight of the aqueous formulation. Preferably, the pH of the aqueous formulations is from about pH 3.0 to about pH 6.5. Most preferably, the pH is about 4.0.

Preferably, the concentration of iodide in the aqueous formulation is from about 0.1 mM to about 200 mM. Preferably, the oxidizing means is present in the aqueous formulation at a concentration from about 0.1 mM to about 200 mM when the oxidizing means is an alkali oxide of iodine or a peracid. Preferably, the oxidizing means is present in the aqueous formulation at a concentration from about 2 µg/ml to about 500 µg/ml when the oxidizing means is a $H_2O_2$ generating enzyme oxidase. Preferably, the glucose oxidase (D-glucose:oxygen 1-oxidoreductase; EC 1.1.3.4) is made up at a specific activity in the range of 2,000 to 200,000 IU per gram of solid, or the diamine oxidase (amine:oxygen oxidoreductase[deaminating] [pyridoxal-containing]; EC 1.4.3.6) is made up at a specific activity in the range of 50 to 800 IU per gram of solid. Preferably, the peroxidase (donor:hydrogen-peroxide oxidoreductase; EC 1.11.1.7) enzyme is present at a concentration of from about 2 µg/ml to about 500 µg/ml when its specific activity is in the range of 250,000 to 330,000 IU per gram of solid.

Preferably, the device is formed into a circular shape suitable for vaginal insertion and retention in the cervical region. Suitable device circular shapes are ring, concave disc, and tampon. Preferably, the circular device has an outer diameter of from about 3.0 cm to about 7.0 cm. Most preferably, the outer diameter is from about 5.6 cm to about 6.0 cm. Preferably, the self-sealing holes are from about 0.01 mm to about 0.15 mm in diameter. Preferably, the self-sealing holes are located about a circumference of the circular shaped device. Most preferably, the density of the self-sealing holes is from about 1 to about 20 holes per $cm^2$ of surface area.

In a sixth embodiment, the present invention provides a microcannular anti-infective and contraceptive device, comprising a solid polymeric material having small channels contained therein and further comprising a dry iodine-generating formulation, wherein the device is formed into a circular shape suitable for vaginal insertion and retention in the cervical region, and wherein the dry iodine-generating formulation is a dry mixture of an iodine salt selected from the group consisting of anhydrous potassium iodide, anhydrous sodium iodide, and combinations thereof, and an oxidizing agent, wherein the oxidizing agent is selected from the group consisting of an anhydrous alkali iodine oxide salt, an inorganic or an organic peracid, a $H_2O_2$ generating oxidase enzyme, and combinations thereof.

Preferably, the concentration of anhydrous potassium iodide, anhydrous sodium iodide, or both is from about 0.5% to about 16% (by weight) of the device. Preferably, the anhydrous alkali iodine salts are selected from the group consisting of sodium iodate, iodine pentoxide, and combinations thereof. Preferably, the inorganic or organic peracids are selected from the group consisting of perborates, organoperoxy acids, and combinations thereof. Most preferably the inorganic or organic peracids, if the only oxidizing agent present in the device, are provided at a concentration of from about 0.5% to about 16% (by weight) of the device. Preferably, the $H_2O_2$ generating oxidase enzyme is selected from the group consisting of glucose oxidase (D-glucose:oxygen 1-oxidoreductase; EC 1.1.3.4), diamine oxidase (amine:oxygen oxidoreductase[deaminating] [pyridoxal-containing]; EC 1.4.3.6), and combinations thereof. Most preferably the $H_2O_2$ generating oxidase enzyme further comprises a peroxidase (donor:hydrogen-peroxide oxidoreductase; EC 1.11.1.7) enzyme. Preferably, the $H_2O_2$ generating oxidase enzyme, if the only oxidizing agent present in the device, is present at a concentration of from about 0.1% to about 2.5% (by weight) of the device. Most preferably, glucose oxidase (D-glucose:oxygen 1-oxidoreductase; EC 1.1.3.4) is present at a concentration of at least 0.5% by weight of the device, wherein the specific activity of glucose oxidase is in the range of 2,000 to 200,000 IU per gram of solid and a peroxidase (donor:hydrogen-peroxide oxidoreductase; EC 1.11.1.7) is present at a concentration of at least 0.01% by weight of the device, wherein the specific activity of peroxidase is in the range of 250,000 to 330,000 IU per gram of solid, with the proviso that the sum concentration of a combination of oxidase and peroxidase (donor:hydrogen-peroxide oxidoreductase; EC 1.11.1.7) enzymes is within the range of from about 0.01% by weight to about 2.5% by weight of the device. Most preferably, diamine oxidase (amine:oxygen oxidoreductase[deaminating] [pyridoxal-containing]; EC 1.4.3.6) is present at a concentration of at least 0.01% by weight of the device, wherein the specific activity of diamine oxidase (amine:oxygen oxidoreductase [deaminating] [pyridoxal-containing]; EC 1.4.3.6) is in the range of 50 to 800 IU per gram of solid, and a peroxidase (donor:hydrogen-peroxide oxidoreductase; EC 1.11.1.7) is present at a concentration of at least 0.01% by weight of the device, wherein the specific activity of peroxidase is in the range of 250,000 to 330,000 IU per gram of solid, with the proviso that the concentration of the $H_2O_2$ generating oxidase enzyme is within the range of from about 0.01% to about 2.5% by weight of the device. Preferably, the microcannular device further comprises a desiccant to stabilize the iodine salts from absorbing moisture from the atmosphere and prematurely solvating and forming free iodine. Preferably, a desiccant is selected from the group consisting of a dry powder mixture of from about 1% to about 10% polyvinylpyrrolidone, $CaCl_2$ and combinations thereof. Preferably, the device is formed into a circular shape suitable for vaginal insertion and retention in the cervical region. Suitable device circular shapes are ring, concave disc, and tampon. Preferably, the device has an outer diameter of from about 3.0 cm to about 7.0 cm. Most preferably, the outer diameter is from about 5.6 cm to about 6.0 cm. Preferably, the solid polymeric material is an elastomeric hydrophobic organosilicon.

Although discussed primarily in terms of elemental iodine producing components, it should be understood that the various embodiments discussed herein may involve the use of alternative anti-infective oxidants, such as those discussed above which are produced in the body. These alternative anti-infective oxidants can be produced from precursor reactants encapsulated in a latent state within a polymer base as a delivery vehicle for the generation and release of the active agents with introduction of a third component essential for activation such as water as a solvating agent, or a co-factor essential for completion of the reaction in the generation of anti-infective products. Thus, for example, alternative oxidants which can be caused to form de novo on demand from precursor reactants include superoxide; hydrogen peroxide; hydroxyl radicals; hypohalites such as hypochlorite ($OCl^-$), hypoiodite ($OI^-$), and hypobromite ($OBr^-$); haloamines including chloramines, iodamines, and bromamines which are the oxidizing products formed through reaction of hypohalites with primary and secondary amines such as taurine chloramine formed by introduction of taurine to hypochlorite; thiocyanogen (($SCN)_2$); hypothiocyanite ($OSCN^-$); and nitric oxide.

DETAILED DESCRIPTION OF THE INVENTION

Figure 1:
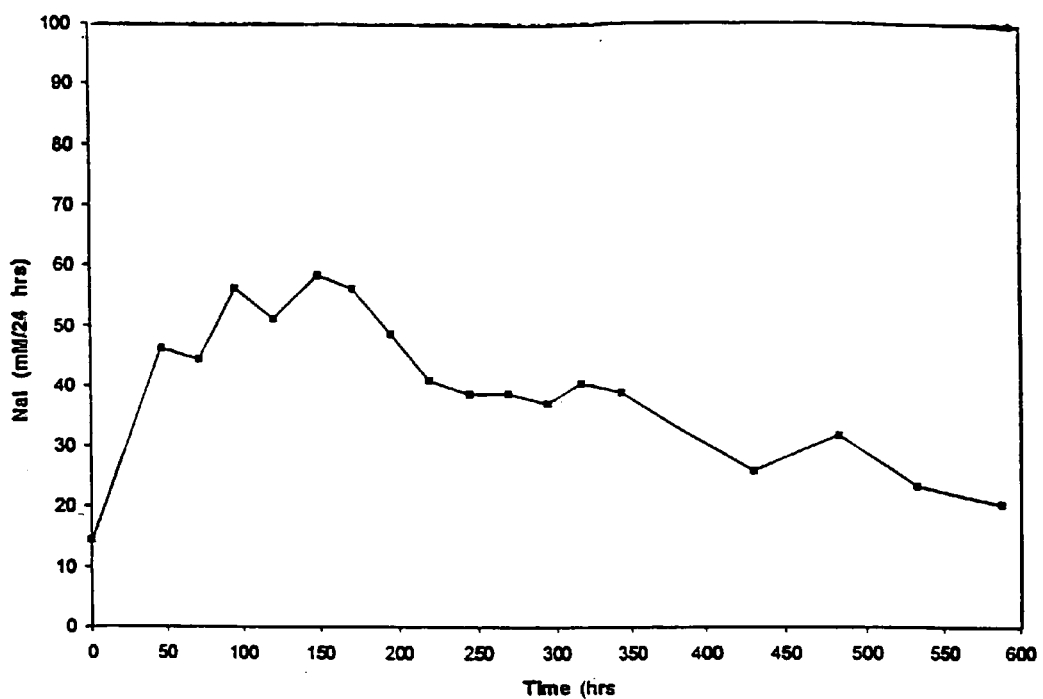
FIG. 1 shows that sodium iodide formulated at a mass ratio of solid to silicone elastomer of ~30% yields a polymeric base on curing which efficiently releases iodide upon immersion and sequential changes in buffer. Iodide peaked at around 50 to 60 mM in a fluid volume of 10 ml buffer per washing interval. The capacity of the fabricated silicone device to restore iodide to this level with sequential changes in buffer remained relatively constant over the first 350 hrs, then declined to ~20 mM by around 600 hrs of continuous immersion and rinsing. Calculations of iodide recovery, relative to iodide initially available in the device, indicated that by 600 hrs of continuous immersion and washing ~90% sodium iodide had leached free of the device.

The present invention provides a medical device having microbicidal, virucidal, and spermicidal activities. In accordance with the invention, the medical devices are an implantable or topical (wound) devices that exhibit microbicidal and virucidal activities through their capacity to generate an oxidant such as elemental iodine over sustained intervals, activated upon submersion of the devices in aqueous fluids. Unlike antibiotic strategies, the incorporation of iodine generating formulations into the devices fabricated out of hydrophobic and/or hydrophilic polymers circumventes the problem of colonizing antibiotic resistant organisms, lending better care and less risk to users of the inventive device for both the prevention and treatment of infections. Although discussed below primarily in terms of elemental iodine as the anti-infective, spermicidal oxidant generated by the medical devices of the invention, it should be understood that other oxidants may similarly be used, as outlined herein.

The inventive process mixes finely ground particles of the oxidant producing compound, such as iodine salts, directly into the polymer base prior to its curing and/or fabrication, as a coating, or as a device, of specific dimensions and configuration. These salts remain inert and trapped within the polymer base until they come into contact with body fluids. The salt mixtures within the microcannulae react with one another upon solvation catalyzing the formation of elemental iodine. A steady supply of nascent elemental iodine was generated over a period of several hours, several days, or weeks depending upon the chemical properties of the polymer base in which the salts were encapsulated, the concentration of salts and reactants relative to the mass of the polymer, and the reactants making up the salt mixture. The inventive device aims to produce an optimal microbicidal killing level of from about 5 to 100 ppm of elemental iodine. Either hydrophilic (water soluble) or hydrophobic (water insoluble) polymer bases can be used in fabricating the inventive device. Anti-infective properties may be conferred to implant devices by coating of prefabricated devices with a layer of hydrophobic or hydrophilic polymers encapsulating elemental iodine generating formulations, or the entire device may be fabricated from polymers encapsulating elemental iodine generating formulations.

The following principles apply in fabricating the inventive device. First, elemental iodine generating formulations must be entrapped in the form of solids within the polymer base in a dormant state until solvated. Second, formation of nascent elemental iodine must occur rapidly, facilitated by maintenance of high concentrations of iodine salts at the solvation site by exploiting oxidation and conversion of iodide into elemental iodine, and by providing a supply of protons within the reaction environment.

The inventive devices (implantable, vaginal treatment and wound dressing) each involve fabrication of anti-infective activity using polymers molded to a specific shape, dependent upon the application required of the device. In incorporating the inventive device into urinary catheters and various other body implant devices, the device prevents acquisition of infections by conferring to the devices in which it is incorporated the capacity to cleanse the site of implantation of pathogenic microbes and viruses. Devices encapsulating various elemental iodine generating formulations can be fabricated for the treatment of acquired infections such as BV, or pPROM, wherein the fabricated device may be configured and placed within the vagina, or against the cervix, to treat such infections. The same device can be fabricated for use as a coating on preformed devices (e.g., orthopedic joints, metal inserts, cardiac pacemakers, etc.), or prepared in the shape of a sheet or "bandaid" as a wound dressing, protecting wounds and burns from infection.

The present invention is based upon the discovery that dry oxidized and reduced salts of iodine can be trapped in hydrophilic and hydrophobic polymers in stable form. When exposed to fluids present in body cavities, such as the vagina, urethra, or in interstitial spaces, the dry oxidized and reduced salts of iodine solvate, and react to form free microbicidal and virucidal elemental iodine. Osmotic gradients established within the device's polymer base, in combination with solvation of the iodine salts and oxidative reactions, account for the sustained formation of nascent elemental iodine. The invention also utilizes natural reducing compounds present in biological fluids (such as in the vagina and other body cavities) for enhancing nascent elemental iodine formation. This is accomplished with chemical forms of iodine encapsulated within the device which are susceptible to reduction, and which can then be caused to oxidize, either nonenzymatically or enzymatically, into nascent elemental iodine.

Hydrophobic silicone polymers encapsulated with iodine salts and its oxides have been fabricated into devices with anti-infective activities. Similar embodiments of the device have been developed using the hydrogels, alginic acid, and polyacrylates, which in fabricated forms can be inserted into various body cavities, or over wounds, where they confer to the treated site microbicidal and virucidal activities.

With reference to the Figures, FIG. 1 shows the capacity of a 5 g block of silicone to release encapsulated sodium iodide. The device was fashioned in the shape of a disc ~0.3 cm thick and 5.0 cm in diameter and sodium iodide was embedded in the hydrophobic elastomer prior to curing. The disk was immersed in an aqueous fluid comprised of 10 mM sodium phosphate, pH 7.4, also made up in 150 mM NaCl. The data in FIG. 1 show the release of sodium iodide over a period of approximately one month.

Figure 2:
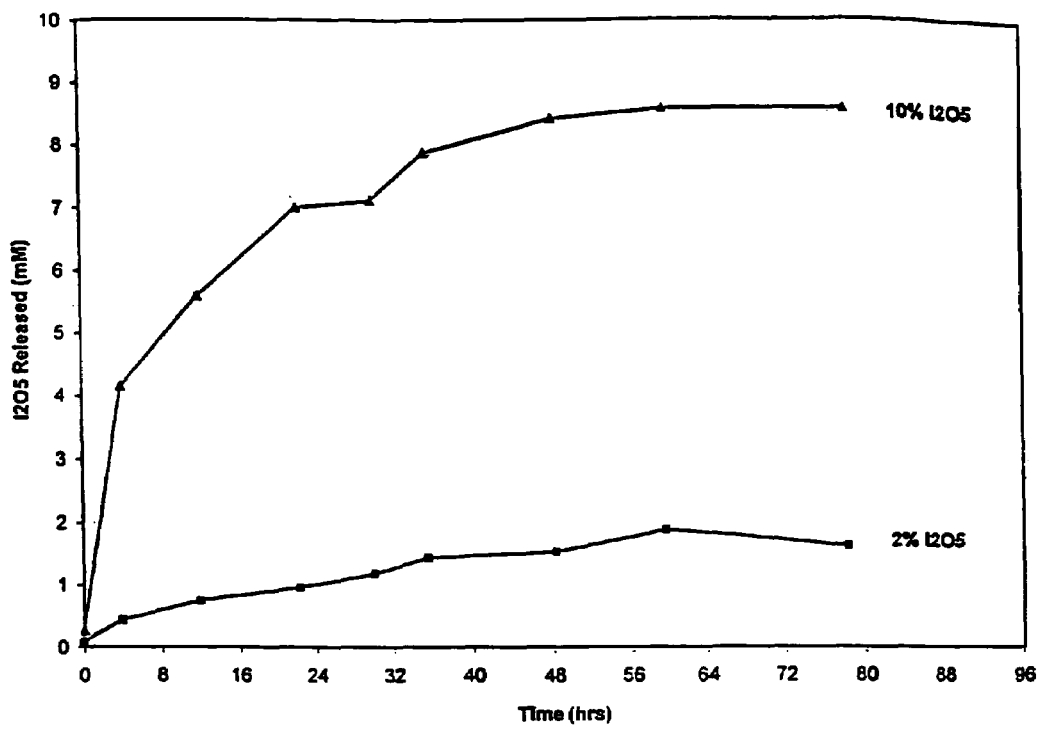
FIG. 2 shows the kinetic release of iodine pentoxide from silicone tablets prepared as in the microbicidal studies summarized in Table 3, and suspended in 100 mM sodium citrate, pH 4.0, at 1 tablet/ml, but using different mass ratios of iodine pentoxide to elastomer. The concentration of iodate released to buffer bathing the tablet can be seen to be proportional to the mass of iodine pentoxide encapsulated within the polymer base. Complex media had no apparent impact on solvation and diffusion rates of iodine pentoxide as identical rates of iodine pentoxide release were observed in substituting BHI media in place of citrate buffer.

FIG. 2 shows that an anhydride of iodate, iodine pentoxide, can likewise be entrapped in microcannulae formed during curing of silicone disc devices fabricated in the same manner as in FIG. 1, but substituting the anhydride in place of iodide. The concentration of the oxide salt released into solution was proportionate to the amount of oxide encapsulated within the silicone polymer prior to curing and fabrication of the device.

Figure 3:
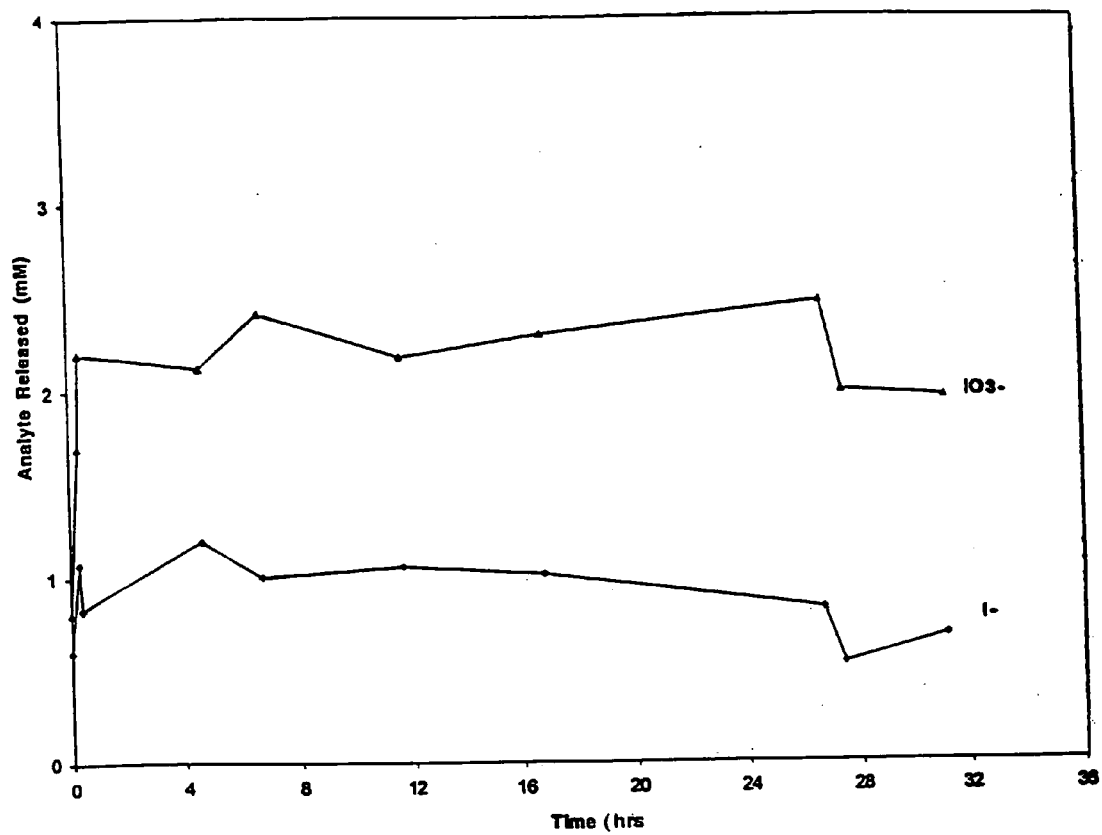
FIG. 3 shows the kinetic release of iodate and iodide at varying intervals after submersion of fabricated tablet formulated by mass with 8% iodate, 2% iodide and 10% PVP, an optimal formulation found effective in killing *C. albicans* when added to BHI at 1 tablet/ml. Tablets were submerged at room temperature in 100 mM sodium citrate, pH 4.0, and aliquots of the buffer then drawn for analysis of iodate and iodide at the intervals indicated. Peak levels of iodate and iodide in the range of 2 and 1 mM, respectively, proved sufficient to catalyze formation of sufficient elemental iodine in the external media to kill *C. albicans* completely in less than 4 hours exposure to the tablets.

FIG. 3 shows that both iodate and iodide may be encapsulated simultaneously within the silicone polymer base during fabrication of a silicone disc device as in FIG. 1. Upon solvation, iodate and iodide react in coming together to form nascent elemental iodine. The presence of elemental iodine was confirmed in the immersion buffer (see FIG. 4), and devices fabricated in this manner were also shown to exhibit potent microbicidal activities (see examples 3 and 4).

Figure 4:
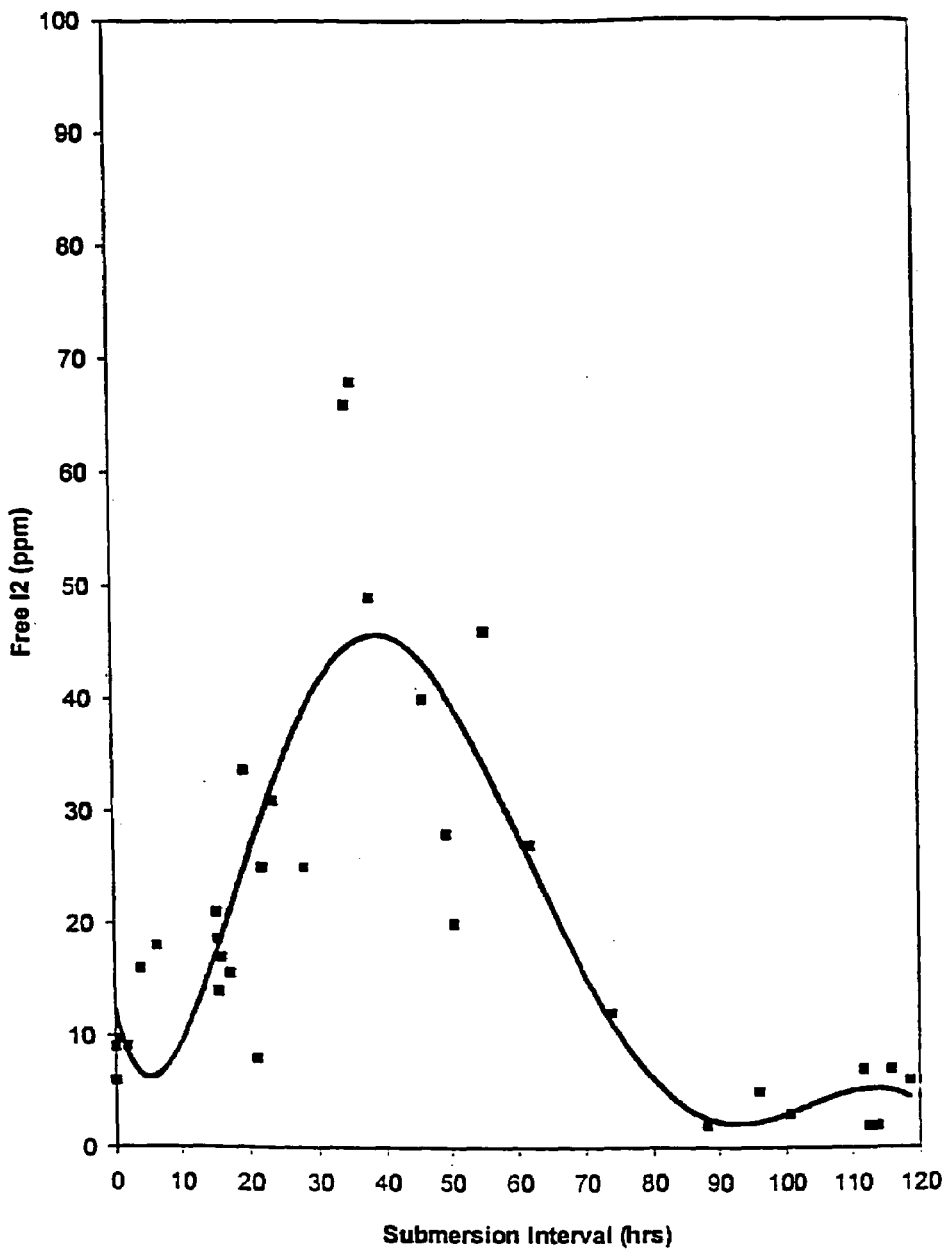
FIG. 4 shows corresponding elemental iodine levels formed in the external medium (100 mM sodium citrate, pH 4.0) at varying intervals of submersion of fabricated silicone tablets (1 tablet/ml) formulated as in examples 3 and 4 at 8% iodate, 2% iodide and 10% PVP by mass relative to the silicone elastomer.

FIG. 4 shows corresponding elemental iodine levels formed in the external medium (100 mM sodium citrate, pH 4.0) at varying intervals of submersion of fabricated silicone tablets (1 tablet/ml) formulated as in examples 3 and 4 at 8% iodate, 2% iodide and 10% PVP by mass relative to the silicone elastomer.

Figure 5:
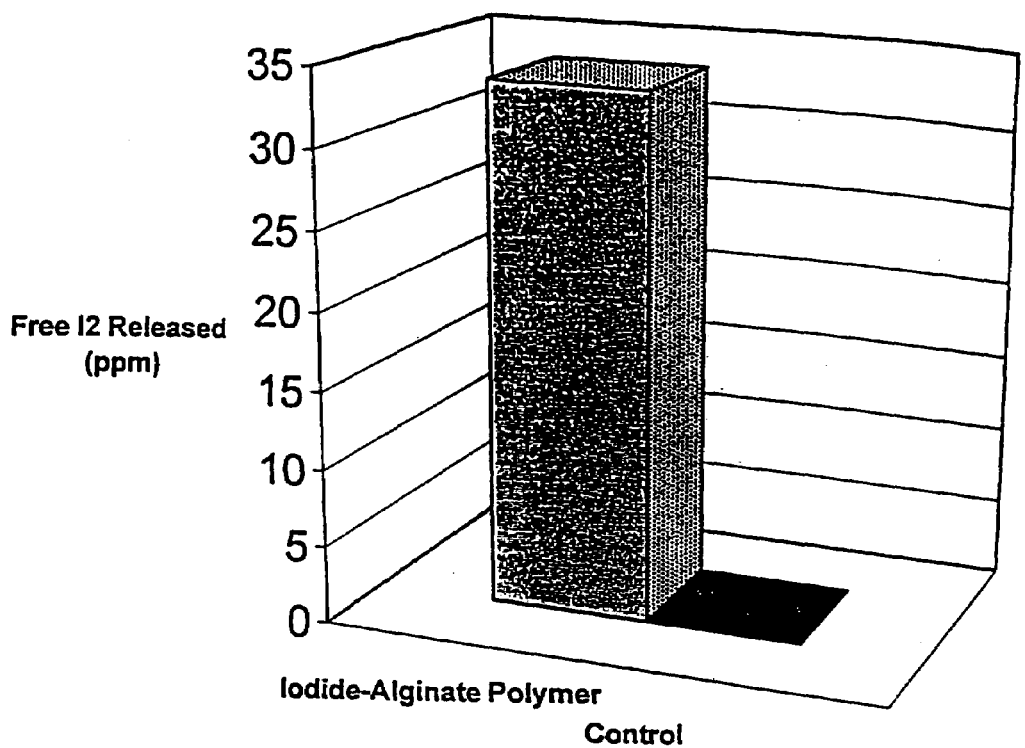
FIG. 5 shows elemental iodine formed de novo with solvation of a 1% high viscosity alginate hydrogel device formulated in 2 mM potassium iodide, 2 mM sodium iodate prior to lyophilization. The lyophilized hydrogel was submerged as a 1 cm×0.6 cm cylindrical section in 1 ml of 100 mM sodium citrate, pH 4.0, and allowed to solvate for 20 minutes before measuring elemental iodine in the buffer medium. Values represent the average of triplicate experiments. The control experiment showed the absence of elemental iodine in sample processed in the same manner, but excluding potassium iodide and sodium iodate from the hydrogel matrix during preparation of the control device.

FIG. 5 shows the release of elemental iodine into immersion buffer (100 mM sodium citrate, pH 4.0) from a hydrogel polymer embodiment. The hydrogel polymer was composed of 1% high viscosity alginic acid and fabricated in the shape of a cylinder suitable for insertion into a wound incision (see example 5). Iodide and iodate was encapsulated within the lyophilized alginic acid polymer. The hydrogel device was activated upon placement of the device in aqueous fluid (i.e., immersion buffer). Upon immersion, the hydrogel solvated and dissipated into the buffer solution so that it was not necessary to remove the device from the site of treatment.

Figure 6:
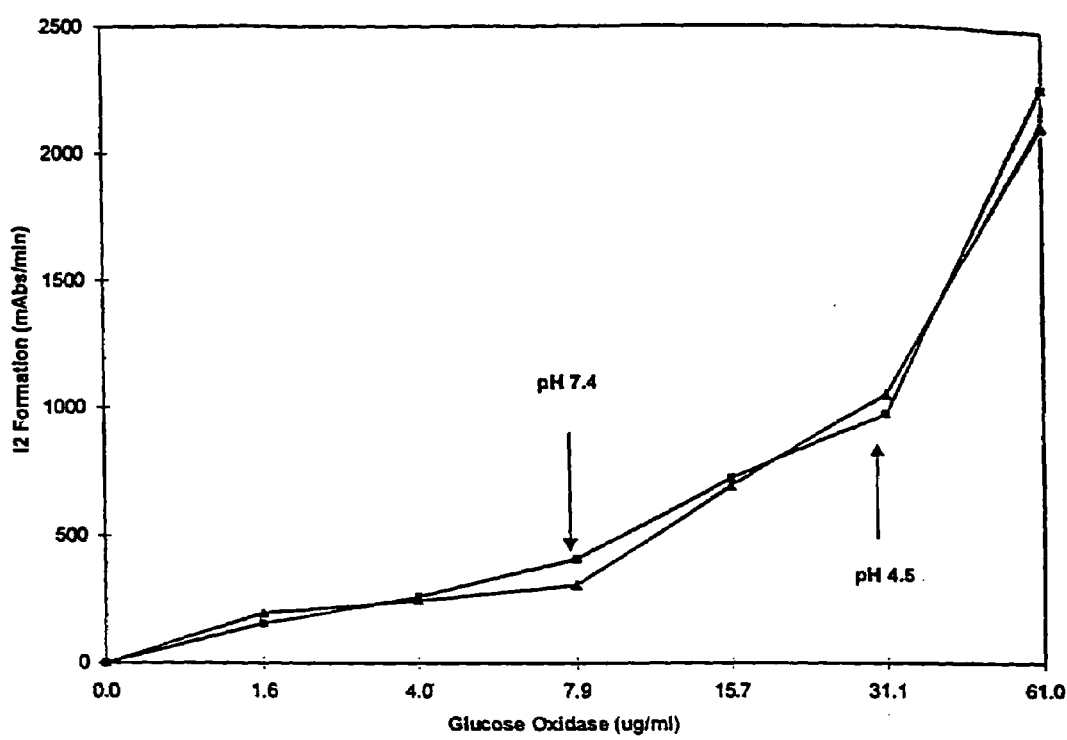
FIG. 6 shows proton driven de novo formation of nascent elemental iodine and demonstrates comparable rates of elemental iodine formation at pH 4.5 versus pH 7.4 using fixed concentrations of horseradish peroxidase, iodide and glucose, and variable levels of glucose oxidase, as indicated.

FIG. 6 shows proton driven de novo formation of nascent elemental iodine and demonstrates comparable rates of elemental iodine formation at pH 4.5 versus pH 7.4 using fixed concentrations of horseradish peroxidase (donor:hydrogen-peroxide oxidoreductase; EC 1.11.1.7), iodide and glucose, and variable levels of glucose oxidase (D-glucose: oxygen 1-oxidoreductase; EC 1.1.3.4), as indicated.

Figure 7:
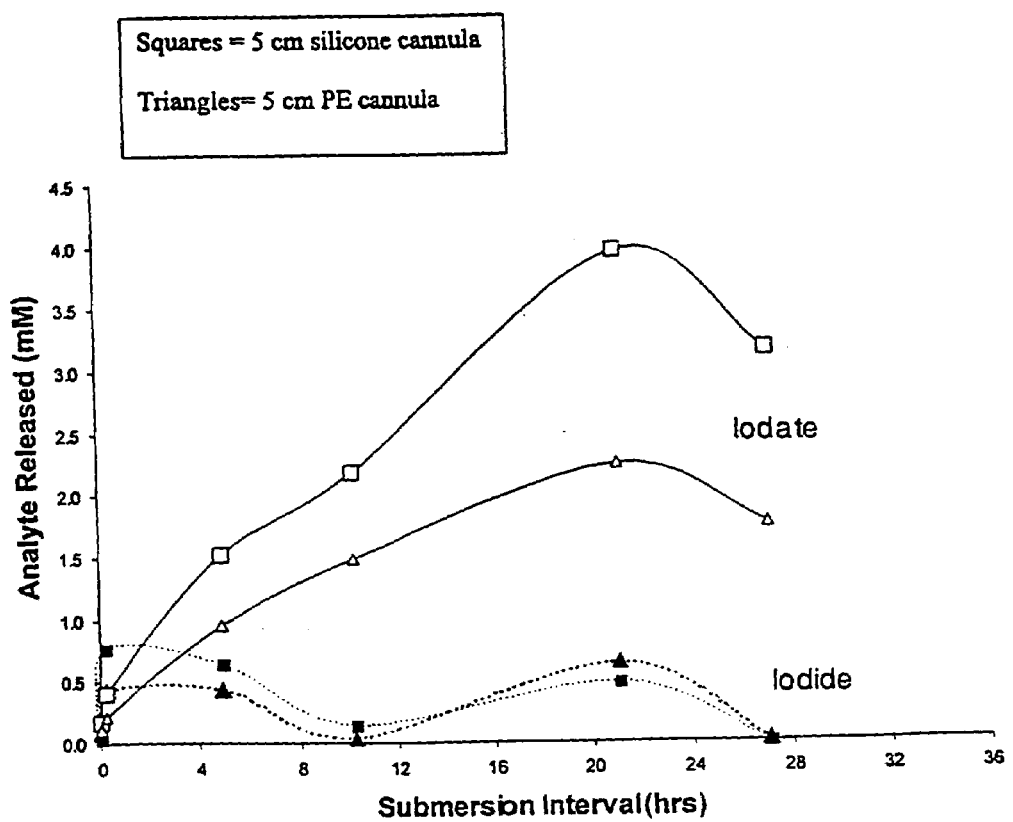
FIG. 7 shows the release of iodate and iodide from silicone and polyethylene coated cannular tubing. The coatings were formulated in 2.5 and 5.0 cm lengths of silicone polymer layered over the cannulae and encapsulated with iodate and iodide made up in PVP (as described in example 6) and with a wall thickness of ~0.1 mm. The polymer-coated cannulae were then immersed in 5 ml of 100 mM citrate buffer, pH 4.0, and aliquots of the buffer solution than periodically analyzed for residual iodate and iodide as indicated over a period of approximately 28 hours. Elemental iodine formed in the wash buffer was also assayed and found to range from a low of ~4 ppm to a high of ~30 ppm over this same interval. Peak levels of iodide and iodate occurred at about 24 hours after submersion of the coated cannulae in the citrate buffer.

FIG. 7 shows the time dependent release of iodide and iodate from strips of polyethylene and silicone cannulae coated with thin layers of silicone polymer encapsulated with an elemental iodine generating formulation comprised of iodide, iodate and PVP (see example 7). The inventive device prototype was submerged in 100 mM sodium citrate buffer, pH 4.0. The average level of nascent elemental iodine formed over the duration of the immersion intervals as a result of the release of iodide and iodate ranged from a low of 4 ppm to a high of 30 ppm.

Fabrication of the Inventive Device

The inventive device contains a reservoir containing an iodine generating formulation designed to produce iodine, when activated, in the range of about 5 to 100 ppm. The inventive device relies upon the presence of specific reducing compounds and/or substrate compounds found in body fluids as "activating agents." Substances present in body fluids and which activate iodine formation from the inventive formulation include reducing compounds such as ascorbic acid, glutathione, and hypotaurine, and substrate compounds such as glucose, and spermine, and water as a solvating agent. The substrate compounds are often coupled with $H_2O_2$ generating oxidase-type enzymes, such as glucose oxidase (D-glucose:oxygen 1-oxidoreductase; EC 1.1.3.4) or diamine oxidase (amine:oxygen oxidoreductase [deaminating] [pyridoxal-containing]; EC 1.4.3.6), for example, and facilitated by a peroxidase (donor:hydrogen-peroxide oxidoreductase; EC 1.11.1.7) such as horseradish peroxidase or lactoperoxidase formulated as a dry powder mixture. This dry powder mixture is encapsulated within the polymer base of the inventive device during fabrication. Upon salvation, the oxidase enzymes come into contact with their respective substrates, thereby triggering formation of $H_2O_2$. The $H_2O_2$ formed as a product of the oxidases acting on their substrate compounds then serves to oxidize iodide (also included in the formulation) into iodine conferring to the device anti-infective (e.g., microbicidal and virucidal), and contraceptive spermicidal, activities. Dry, finely ground oxides of iodine salts, peracids, or comparable oxidizing agents (e.g., perborate, peracetate, etc.) can be substituted in place of the oxidase enzymes in formulations entrapped within the inventive device.

In the oxidative conversion of iodide into iodine, a wide array of oxidants, i.e., oxidizing agents, may be employed so long as they can be formulated into an anhydrous powder. Thus, the oxidants remain immiscible upon addition to the hydrophobic polymer used in fabricating the delivery device, and they retain the capacity to solvate upon immersion in aqueous fluids so that they can come into contact with iodide, and thereby cause its conversion to iodine. In this case of sodium iodate, or iodine pentoxide (which spontaneously hydrolyzes to iodate), crystalline salts become entrapped in microcannulae of the delivery device and egress from the device upon coming into contact with body fluid such as vaginal fluid. The crystalline salts react with reducing compounds present in the vaginal fluids and semen, resulting in elemental iodine formation in accordance with redox reactions involving iodine chemistry. Hence, the use of iodate in formulations exploits the reducing environment in which the device resides to allow for elemental iodine formation to ensue, bathing the vaginal walls and cervix in spermicidal and microbicidal iodine activity (e.g., from 5 to 100 ppm).

For incorporation of formulations into hydrophobic polymers, fabrication of the inventive device requires that the iodine-generating formulation first is ground to a fine powder of 200 micron, or less. The dry formulation is then mechanically mixed at room temperature (20 to 25° C.) into a hydrophobic elastomer used as the polymer base in fabricating the device to form a mixture. Variations in producing master batches prior to curing in the final polymer base are amenable to the technology. For example, the anti-infective oxidant generating component such as potassium iodide, may be premixed in one co-polymer (Part A). The proton source such as monosodium phosphate and an oxidizing agent such as sodium iodate can then be mixed into the other co-polymer crosslinking agent together with an appropriate catalyst (Part B). To cure the polymer, Part A and Part B may then be mixed together allowing for initiation of the crosslinking polymerization process concomitant with encapsulation of the iodine-generating formulation within the final mixture. Before the mixture has cured, the mixture may then be delivered to a mold, or extruded from a dye, and allowed to cure to its final configuration. The shape of the device is suitable for its site of application. Suitable configurations include extruded sheets to be layered over wounds and burns for the prevention and treatment of surface infections, formation of rings and tampons for the treatment and/or prevention of vaginal infections, or pPROM, fabrication in the shape of a Foley catheter for the prevention of urinary tract infections and formation of a self-sterilizing urinary catheter, extrusion as a covering over a catheter lead wire in conferring to the latter anti-infective properties, etc. The intended use in a particular body cavity or wound site determines the appropriate shape.

Suitable hydrophobic polymers (elastomers) to be used in fabrication of the inventive device include, for example, medical grade Low Consistency Silicone elastotmers (LSR silicone elastomers) such as NuSil MED-4815, -4820, -4830, -4840 or -4850 molding materials, NuSil medical grade LSR4-5805 silicone elastomer, High Consistency Silicone Elastomers (HTR elastomers) suitable for extrusion such as NuSil MED-4550, -4565, -4719, -4750 and -4780, as well as thermoplastic and room temperature vulcanization silicone polymers. Other suitable polymers include elastomers such as polyurea, polyurethane, ethylene vinyl acetate, polyvinylchloride, polyesters, polyamides, polycarbonate, polyethylene, polymethyl methacrylate, cellulose esters such as ethyl, methyl and propyl forms, polypropylene, polystyrene, polytetrafluoroethylene, poly(ethylenevinyl acetate), elastomeric organosilicon polymers, poly(hydroxyl alkyl esters), copolymers and thermoplastic hydrophobic combinations thereof.

For formulations encapsulating enzymes such as glucose oxidase (D-glucose:oxygen 1-oxidoreductase; EC 1.1.3.4) or diamine oxidase (amine:oxygen oxidoreductase[deaminating] [pyridoxal-containing]; EC 1.4.3.6), room temperature vulcanization elastomers must be used in fabricating the device from hydrophobic polymers since enzymes will denature using the higher temperatures required in curing thermoplastic polymers. The higher curing temperatures, in the range of from 120 to 170° C., pose no problem for entrapment of nonenzymatic components of the formulations used in fabricating this device. The free level of iodine formed at the surface of the device upon wetting the device in body fluid should preferably reach a level not less than ~5 ppm, or in excess of 100 ppm within 20 minutes of its exposure to body fluid. This level of elemental iodine is highly desirable to confer to the device microbial, virucidal and spermicidal activities.

Alternatively, the inventive device may be fabricated from a hydrophilic (e.g., hydrogel) polymer. In this embodiment, the polymer base serves to encapsulate the iodine generating formulation and solvates concomitantly with activation of the iodine generating formulation as a gel-sol, mucoid-like product, coating and bathing the implant site with anti-infective activity.

Suitable hydrogels for mixing into formulations include, for example, from about 0.2 to 5% high or medium viscosity alginic acid, B.F. Goodrich Carbopol 971 PNF (or crosslinked analogues of this polyacrylic acid such as B.F. Goodrich Carbopol 974 PNF or Noveon™ AA1), or about 1:1 mixtures of alginic acid and Carbopol, adjusted from to a preferred pH of about 3.7 to 4.2 with NaOH. Several classes of hydrogels are amenable to this embodiment, in general, including hydrogels selected from groups consisting of linear or cross-linked polyacrylates, polycarboxyalkyl celluloses, hydroxyalkyl celluloses, water soluble celluloses, polyethylene or polyvinyl alcohols, chitosan polymers, as well as salts of alginic acids and combinations thereof.

Providing for a low pH in the hydrogel embodiment of the device is important in ensuring a steady supply of $H^+$ in forming elemental iodine (see example 6). Additionally, in the embodiment in which the device is used intravaginally, the low pH of the hydrogel is important in maintaining the pH of the vaginal fluid at its normal pH (e.g., ranging from about 3.7 to 4.5). The low pH has an additional advantage in that it also confers some spermicidal and microbicidal activity to the hydrogel formulation. The hydrophilic polymers (e.g., hydrogels) containing the elemental iodine generating formulations must first be premixed at low temperatures near the freezing point of water. They can then be transferred to a mold, and frozen and lyophilized to remove water, forming an anhydrous, stable formulation, preferably in the shape of a disc, that can be manually inserted into the vagina against the base of the cervix. This process of freezing and then lyophilizing the formulation yields a sponge-like product capable of producing microbicidal and virucidal levels of nascent elemental iodine upon introduction to body fluids. Upon insertion into the vagina, the disc solvates to a thick gel, adhering tightly to the vaginal and cervical epithelium with the consistency of a thick mucous-like substance, releasing the active ingredients by which elemental iodine can then be formed. The anhydrous, stable formulation can be stored in desiccated form without loss of iodine generating activity.

Iodide and oxidizing agents of iodide such as iodate salts, or enzyme oxidases such as glucose oxidase (D-glucose: oxygen 1-oxidoreductase; EC 1.1.3.4) and peroxidase (donor:hydrogen-peroxide oxidoreductase; EC 1.11.1.7), may be mixed together and formulated into a single hydrogel formulation, or the iodide and oxidizing agents may be cast in separate hydrogel formulations, and, once recovered in lyophilized form, reassembled as a bilayer of iodide and oxidizing agent.

The freeze-drying technique for fabrication of the hydrogel embodiment of the inventive device allows for fabrication of a dissolvable, anti-infective, spermicidal, hydrogel formulation. The sponge-like hydrogel product can be pressed into sheets, or rolls, and cut into various shapes, by placing the lyophilized hydrogel product in a hydraulic press and applying a pressure of not less than 100 lbs per square inch, nor more than 12,000 lbs per square inch to the final product. This yields a fine, paper-like product which can be cut and shaped as desired, and which upon wetting rehydrates to a gel solution.

A hydrogel device is formed into varying shapes (sheets) for application to an infected site by layering one hydrogel sponge product containing iodide on top of a second containing the oxidizing agent required to trigger formation of elemental iodine to form a composite sandwich product, placing the composite sandwich product into a hydraulic press, and applying pressure to the two layers stacked one on top of the other to form a bilayer membrane. The wetting of the latter sandwich product results in salvation of the hydrogel sandwich, and concomitant production of anti-infective iodine.

Figure 8:
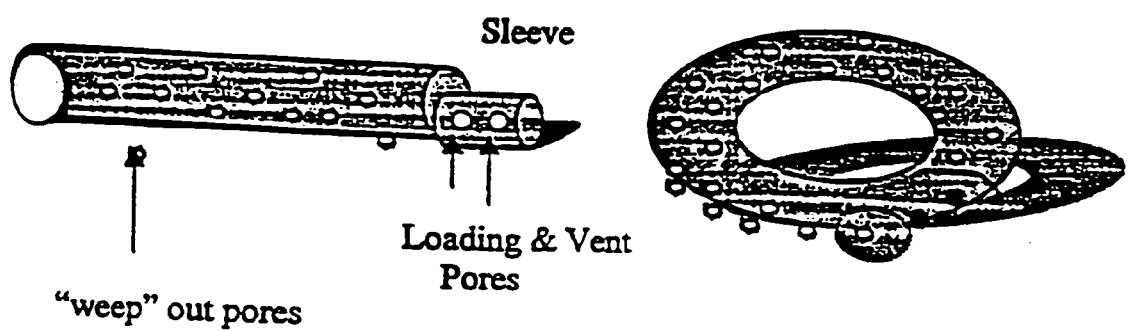
FIG. 8 shows two configurations of the inventive mechanical-release device in an unfolded (left) and ring (doughnut) configuration (right) for insertion into the vagina against the cervix.

In another embodiment, a mechanical-release device is provided which releases oxidant generating formulations, such as iodine generating formulations, contained within an interior reservoir of the device. Operation of the mechanical-release device involves addition of iodide and/or its oxides, with or without reducing substrates, substrate compounds, inorganic or organic oxidizing agents, or $H_2O_2$ generating enzymes within an interior chamber defined, for example, by silastic (silicone) tubing. Preferably, the silastic tubing is formed as a ring shape so that it may be seated at the formix between the cervix and vaginal wall (FIG. 8). Preferably, the diameter of the outer ring is from about 5.8 to about 6.2 cm. Preferably, the tubing is perforated with a series of self-sealing holes of approximately 0.01 to 0.1 mm diameter, dispersed relatively uniformly about the circumference of the tubing (that is toward to outside, as opposed to the inside, of the ring-like structure) at a density of from about 1 to about 20 holes per $cm^2$. The holes allow for release of the iodine generating formulation only during compression and distortion of the tubing through flexing, stretching and rotational motion occurring during sexual intercourse as a result of spontaneous muscular contractions initiated at the base of the cervix during arousal and intercourse. The holes in the tubing are sufficiently small so that the "elastic memory" of the silastic tubing seals formulation within the inner reservoir of the device when the tubing is in a relaxed, or in an undistorted state, retaining the contents held within the inner core reservoir (e.g., the lumen of the tube), preventing mixing of elemental iodine generating formulation within the inner reservoir from presentation to the vaginal walls and cervix in the vicinity of the cervical os. Thus, only during vigorous distortion of the ring through muscular contractions (as occurs during sexual arousal and intercourse) can the iodine generating formulation contained within the interior chamber of the tubing egress, or "weep", to the external surface of the delivery device. Upon contact with the external surface of the device, the formulation provides, essentially, an "on demand" formation of iodine. Moreover, once outside the inner reservoir, the formulation responsible in generating elemental iodine can be caused to smear across and coat the cervix and vaginal walls during intercourse, thereby creating a chemical barrier across which bacteria, viruses and sperm cannot penetrate. Thus, the source of elemental iodine in a preferred embodiment is presented only "on demand" during sexual arousal and intercourse. By devising the delivery system so that it can be caused to activate at the time of sexual arousal and intercourse, appropriate concentrations of elemental iodine, in the range of 5 to 100 ppm, for both spermicidal and anti-infective activities, can be formed locally at the time they are needed. The user does not need to time intercourse closely with application of the contraceptive agent. In addition, by the design of "on demand" delivery of elemental iodine, the effectiveness of this birth control method is enhanced because it does not call upon the attention of the user to time and carefully orchestrate use of the device in order for it to work effectively at the time of sexual arousal and intercourse.

During the manufacture of the mechanical "on demand" release device, the silastic tubing is produced in an elongated configuration in which two holes (having a diameter of from about 0.20 to about 0.25 cm) are placed adjacent to one another, from 0.3 to 0.4 cm distance apart, in a straight line from one another along the longitudinal axis of the tubing, and located on a sleeve fabricated into the tubing (FIG. 8). One hole serves as an air vent for allowing air to escape the reservoir during loading of the device with the iodine generating formulations. The other serves as the inlet hole by which the formulations are delivered into the inner reservoir of the tubing.

To load the device, the end of the tubing containing the sleeve is inserted into the opposite open end of the tubing, leaving the air and vent holes exposed, and bringing the device into the shape of a ring (FIG. 8). The formulation to be placed in the device is then delivered by means of a tapered "eye dropper" dispensing bottle designed so that the pointed dispensing end fits into the inlet hole. Eye droppers, or any cone shaped pipetting tip small enough to pass into the delivery inlet-hole will suffice in loading formulations into the device. Formulations for generating elemental iodine are loaded through the inlet hole while holding the ring in a position so that fluid will not spill out the vent hole as the reservoir is loaded. Fluid can be loaded into the ring until the last air bubble appears at the air vent hole. At this point, the ends of the tubing joined to one another through the sleeve fitting are pushed tightly together causing the opposite end of the tube lacking the sleeve to slide over the inlet and air vent holes, thus closing off any possibility of fluid escaping back out of the inlet loading and air vent holes, and forming a tightly sealed delivery device (FIG. 8) ready to be placed manually at the base of the cervix such that it surrounds the cervix and sits snugly between the formix and vaginal wall.

In the fully closed ring configuration, formulations loaded into the device necessary in catalyzing formation of elemental iodine can no longer escape except through the small "weep" holes distributed about the circumference of the tubing. These weep holes are self-sealing in the same fashion as a serum septum cap retains self-sealing properties after being punctured by a 20 to 21 gauge needle, yet they allow the formulation loaded into the device to "weep" out as the tubing is stretched and distorted. It is important that the diameter of the "weep" holes not be too large to render the silastic tubing leaky, resulting in the loss of formulation before the device can be properly inserted into the vagina, and at inappropriate times outside periods of sexual arousal and intercourse. While the above description focuses on a tube-type chamber, other configurations are also applicable wherein the basic elements of the mechanical release device entail a flexible, self-sealing wall, and inner hollow, from which iodine generating formulations may be caused to "weep" through distortions in the walls of the device caused during sexual arousal and muscular contractions occurring during sexual intercourse.

Formulations

In both the mechanical-release and the hydrogel delivery device, similar iodine generating formulations are used. In both instances the formulations are prepared in a lyophilized, anhydrous state containing a hydrogel to provide body (viscosity) to the formulation, and to render it stable for storage until required for use. In the case of the mechanical-release device embodiment, the formulation is, in principle, hydrated by the addition of a defined quantity of water before use to bring the ingredients to their stated concentrations made up prior to lyophilization of the formulation. It is feasible to prepare the lyophilized formulation so that it is inserted within the mechanical-release device such that water is the only ingredient required in reconstituting the formulation through addition to the mechanical-release device, added through the loading port hole (FIG. 8). Alternatively, the formulation can be prepared in a lyophilized form within a separate loading container, such as a plastic bottle with a tapered tip. The tapered tip is preferred for loading its reconstituted formulation contents into the delivery device. On the other hand, the hydrogel delivery device is preferably formed in a lyophilized state for direct insertion into the vagina and relies upon body fluids for solvation and release of the iodine generating formulation. Hence, it requires no addition of water or other aqueous solvent to reconstitute it before its insertion and use within the vagina.

Reconstituted aqueous formulations are comprised of iodide, wherein the iodide is selected from the group of potassium iodide, sodium iodide and combinations thereof, an oxidizing agent, wherein the oxidizing agent is selected from the group consisting of alkali iodine oxide salts such as sodium iodate, iodine pentoxide, other inorganic or organic oxidizing agents, peracids (e.g., perborate, peracetate, etc.), and combinations thereof. Alternatively, the oxidizing agent is replaced by $H_2O_2$ generating enzyme oxidases, such as glucose oxidase (β-D-glucose:oxygen 1-oxidoreductase; EC 1.1.3.4) or diamine oxidase (amine:oxygen oxidoreductase [deaminating] [pyridoxal-containing]; EC 1.4.3.6), facilitated by the addition of peroxidase (donor:hydrogen-peroxide oxidoreductase; EC 1.11.1.7), and combinations thereof. The concentration of iodide in the aqueous formulations should be not less than about 0.1 mM or more than about 200 mM. The oxidizing agent acting on iodide may be chosen from alkali oxides of iodine such as sodium iodate, or iodine pentoxide, or peracids made up in solution prior to lyophilization and reconstitution to not less than 0.1 mM nor more than 200 mM.

Alternatively, $H_2O_2$ generating enzyme oxidases may be substituted in place of the inorganic or organic oxidizing agents. Glucose oxidase, for example, may be made up in solution prior to lyophilization at a concentration of at least 2 μg/ml wherein its specific activity is in the range of 2,000 to 200,000 IU per gram of solid. Peroxidase may be incorporated into the formulation to facilitate the oxidative conversion of iodide to iodine made up at a concentration of at least 2 μg/ml, wherein its specific activity is in the range of 250,000 to 330,000 IU per gram of solid, or diamine oxidase (amine:oxygen oxidoreductase[deaminating] [pyridoxal-containing]; EC 1.4.3.6) may be substituted in place of glucose oxidase made up to at least 2 μg/ml wherein its specific activity is in the range of 50 to 800 IU per gram of solid, or any combination thereof.

In addition to these reactive ingredients, the formulations are optionally supplemented with a hydrogel agent, wherein the hydrogel agent is selected from the group consisting of linear polyacrylates, cross-linked polyacrylates, polycarboxyalkyl celluloses, polyalkyl celluloses, hydroxyalkyl celluloses, water soluble celluloses, polyethylene or vinyl alcohols, chitosan polymers, salts of alginic acids, and combinations thereof. The hydrogel is preferably made up to not less than about 0.2% (by weight) in water, nor more than about 5% by weight. Preferably, the hydrogel is about 2% by weight of the composition. Preferably, the pH is adjusted to a range of not less than about 2.0 and not greater than about 6.5. Most preferably, the pH is about 4.0. Examples of specific hydrogels suitable for use include cross-linked polyacrylates, such as Polycarbopol 974 PNF or Noveon™ AA1 (B.F. Goodrich), crab shell solubilized chitosan (poly-[1→4]-β-d-glucosamine), carboxyethyl- and methyl cellulose polymers, and sodium salts of alginic acid (ranging from high to medium viscosity −2% solution at 25° C. equivalent ranging from 14,000 cps to 3,500 cps, respectively).

In fabricating the inventive device from hydrophobic polymers, the same basic iodine generating formulations used in hydrogel delivery devices, excluding hydrogels in the final formulations, and water (aqueous solvent or salts thereof), can be used. Formulations are mixed and slurried into hydrophobic polymers used in fabricating the device in the form of anhydrous powders, ground to less than 200 microns, which after mixing and curing, form microcannula within the fabricated device from which the ingredients can then react upon solvation with exposure of the device to body fluids. Suitable hydrophobic elastomers for encapsulation of the iodine generating formulations include polyurea, polyurethane, ethylene vinyl acetate, polyvinylchloride, polyesters, polyamides, polycarbonate, polyethylene, polymethyl methacrylate, cellulose esters such as ethyl, methyl and propyl forms, polypropylene, polystyrene, polytetrafluoroethylene, poly(ethylenevinyl acetate), elastomeric organosilicon polymers, poly(hydroxyl alkyl esters), copolymers and thermoplastic hydrophobic combinations thereof, wherein the dry iodine-generating component is a dry mixture of an iodine salt selected from the group consisting of anhydrous alkali iodine salts such as potassium or sodium iodide at a concentration of from about 0.01% to about 16% (by weight), and an oxidizing agent, wherein the oxidizing agent is selected from the group consisting of anhydrous alkali iodine oxide salts such as sodium iodate, or iodine pentoxide, or a peracid or its salt, such as perborate, organoperoxy acids, and the like, at a concentration of from about 0.01% to about 16% (by weight). Alternatively, a $H_2O_2$ generating enzyme oxidases may be used, such as glucose oxidase (D-glucose:oxygen 1-oxidoreductase; EC 1.1.3.4) or diamine oxidase (amine:oxygen oxidoreductase [deaminating] [pyridoxal-containing]; EC 1.4.3.6), and facilitated by peroxidase (donor:hydrogen-peroxide oxidoreductase; EC 1.11.1.7), and combinations thereof at a concentration of from about 0.01% to about 1.5% (by weight), whereby with solvation of the dry mixture and egress from the device, iodine is formed.

Polyvinylpyrrolidone, $CaCl_2$, or other desiccants may be added to the formulations to improve the stability of the encapsulated formulations. The iodine oxides, in combination with iodide, are hydroscopic and can draw moisture from the atmosphere into the microcannulae of the device leading to premature release of iodine generating activity. From 1% to 10% powdered polyvinylpyrrolidone by elastomer weight, or a comparable amount of an alternate crystalline desiccant, such as $CaCl_2$, included in the formulation, alleviates premature release of elemental iodine from the fabricated device.

In the inventive device, specific reducing compounds or substrate compounds present in biological fluids can be exploited in promoting the formation of nascent elemental iodine through the design of the elemental iodine generating formulations entrapped within the microcannula of the (hydrophobic) polymer base. Substances in vaginal fluids, for example, and which can be used to enhance nascent elemental iodine formation, include reducing compounds such as ascorbic acid, glutathione, and hypotaurine, and the substrate compound glucose.

A substrate compound (such as glucose) coupled with an oxidase-type enzyme (e.g., glucose oxidase (D-glucose: oxygen 1-oxidoreductase; EC 1.1.3.4) when glucose is a substrate), and a peroxidase (donor:hydrogen-peroxide oxidoreductase; EC 1.11.1.7) (such as horseradish peroxidase) is formulated as a dry mixture. The dry mixture is encapsulated within a hydrophobic polymer base along with iodide. Such a formulation illustrates exploitation of reducing equivalents present in body fluids as a source of generating nascent elemental iodine. Upon solvation, the oxidase and peroxidase enzymes in the formulation come into contact with glucose (from a biological fluid), triggering formation of hydrogen peroxide ($H_2O_2$) as a product of glucose oxidase acting on glucose. $H_2O_2$ serves as a substrate in combination with iodide anion (also included in the formulation) to convert iodide into nascent elemental iodine via peroxidation by horseradish peroxidase (donor:hydrogen-peroxide oxidoreductase; EC 1.11.1.7). The same formulation can be used for devices fabricated out of hydrogels coming into contact with whole blood, serum or serum transudates, and various other body fluids, where glucose can be found in abundance and harnessed through the glucose oxidase and horseradish peroxidase reaction to catalyze nascent formation of elemental iodine.

It should be noted that the glucose oxidase/horseradish peroxidase elemental iodine generating formulation confers substrate (i.e., glucose) specificity to the inventive device. In the absence of glucose (such as when the device is stored) in the polymer formulation the formulation cannot catalyze formation of nascent elemental iodine because glucose is an essential first step component of the chemical reactions leading to elemental iodine formation. This particular formulation allows for the device to activate and lay down anti-infective activity only upon contact with body fluids containing glucose. Even exposure to water does not active the release of iodine.

The hydrogel delivery device may be used to deliver iodine-generating formulations without the necessity of removing the device from the body region, such as the vagina, following its use. Instead, it solvates to a gel-sol, mucoid-like product, which coats the cervix and vaginal walls, and lays down an impenetrable spermicidal and microbicidal barrier of elemental iodine lasting from 8 to 24 hours following its insertion intravaginally, and dissipates slowly from the vagina over a period of days as normal mucoid-like fluid escaping the introitus. An example of an indication best suited for the use of a hydrogel inventive device is for the treatment of BV. In this instance, the device is cast in liquid hydrogel form into a flattened disc shaped mold with a diameter of from 4.5 to 5.5 cm, and a thickness of 0.3 to 0.7 cm. Variations in the diameter of the disc, or the general shape of the device (e.g., concave discs, tampons, etc.) may be made in certain instances to accommodate differences in the anatomy of some vaginas. This design was chosen to allow the disc to be inserted into the vagina against the base of the cervix. The disk-shaped hydrogel device, once inserted, will egress microbicidal activity concomitant with solvation and coat the cervix and vaginal walls with a thin layer of the elemental iodine generating formulation encapsulated within the solvated hydrogel. Examples of suitable hydrogel polymers include, for example, from 0.5 to 2% high or medium viscosity alginic acid, B.F. Goodrich Carbopol 971 PNF (or crosslinked analogues of this polyacrylic acid such as B.F. Goodrich Carbopol 971 PNF or Noveon™ AA 1), or 1:1 mixtures of alginic acid and Carbopol, adjusted from a pH of about 3.7 to 4.2 with NaOH. The low pH of the hydrogel is important in providing $H^+$ which are consumed in forming nascent elemental iodine (see example 8), and in maintaining the pH of the vaginal fluid at its normal pH (e.g., ranging from about 3.7 to 4.5). The low pH has an additional advantage in that it also confers some microbicidal activity to the hydrogel formulation.

Critical fabrication steps of the hydrogel device to encapsulate the elemental iodine generating formulations include:

(1) prechilling the gel-forming solution to less than 4° C. but not below freezing temperatures; (2) adding and mixing in an elemental iodine generating formulation into the gel solution, (3) casting the mixture into a mold; and (4) rapidly freezing and lyophilizing the mixture. The final product contains the elemental iodine generating compounds encapsulated within the desiccated fibers of the hydrogel in a dormant state. Upon insertion and contact with body fluids (for example, vaginal fluids), the device spontaneously generates elemental iodine as a result of the release of the elemental iodine generating compounds into solution concomitant with solvation of the hydrogel polymer.

An alternative method of manufacturing the hydrogel device without use of a mold is to cast the hydrogel premixed with elemental iodine generating formulations in sheets of from about 0.3 to about 0.5 cm thick, lyophilize the sheets, and then trim the sheets to the desired shape. Trimming is done with any suitable shearing device, knife or blade.

The following example illustrates fabrication of a specific embodiment of the inventive device in the form of a hydrogel membrane containing anti-infective properties upon solvation in body fluids. A 2% (by weight) "medium viscosity" sodium alginate in distilled water was made up and mixed with an equal volume of 2% Carbopol 971 (B.F. Goodrich) made up in distilled water to yield a composite 1% viscous gel solution, pH 3.95, made up of equivalent weights of alginate and Carbopol. The viscous gel solution was chilled to about 4° C. and 100 mM potassium iodide in water was added and mixed thoroughly to yield a final concentration of from about 1 mM to about 5 mM potassium iodide. A similar gel mixture using 100 mM sodium iodate made up in water was prepared to yield an equal volume of from about 1 to about 5 mM sodium iodate. The two gel mixtures were prechilled to less than 2° C. and then rapidly mixed together. The combined gel mixtures were cast in a flat bed plastic tray prechilled below 0° C. The cast mixture was then plunged into a −70° F. freezer so that the colloid mixture quickly froze into a solid sheet. The total process procedure, from the time of mixing the iodide and iodate gel mixtures together until they are frozen solid as a sheet, should not exceed from 3 to 5 minutes. Once frozen, the sheet was transferred to a lyophilizer to sublime off the water under high vacuum using a vacuum pump. The final product was a fine, highly porous, lightweight, sponge-like sheet (approximately 0.3 to 0.5 cm in thickness), red-brown to slightly purple in color. Once lyophilized, the sheets can be cut, or pressed under a hydraulic press, into varying shapes as desired such as a circular disc of from about 4.5 to about 5.5 cm in diameter for vaginal delivery, for example, such as for an indication to treat BV.

Other shapes, such as cylinders, square films, etc. may be cut from the desiccated sheets as desired. An inventive hydrogel device, as described herein, will form nascent elemental iodine within the range of from 5 to 100 ppm, and within seconds of coming into contact with body fluids. Elemental iodine formed in the hydrogel device dissipates over a period of from approximately 4 to 12 hours after activation of the device (e.g., after initiation of free elemental iodine formation has occurred).

A variation of the this process for forming inventive hydrogel devices in the form of a membrane involves mixing either glucose oxidase (D-glucose:oxygen 1-oxidoreductase; EC 1.1.3.4) (from about 10 to about 500 $\mu$g/ml) or horseradish peroxidase (donor:hydrogen-peroxide oxidoreductase; EC 1.11.1.7) (from about 2 to about 20 ug/ml) or both in from about 0.5 to about 2% alginate-Carbopol gel solution made up in water at room temperature. Potassium iodide is then added to this mixture to a final concentration of from about 1 to about 10 mM. This hydrogel mixture is then frozen and lyophilized in sheets as described above for the iodide/iodate hydrogel mixture. The final sponge-like product has an off-white color, and can be stored at room temperature without loss of nascent elemental iodine generating activity. Upon insertion into body fluids containing glucose, the inventive hydrogel device solvates within 5 to 20 minutes concomitantly producing elemental iodine within the solvated gel mixture in the range of 5 to 100 ppm.

Figure 10:
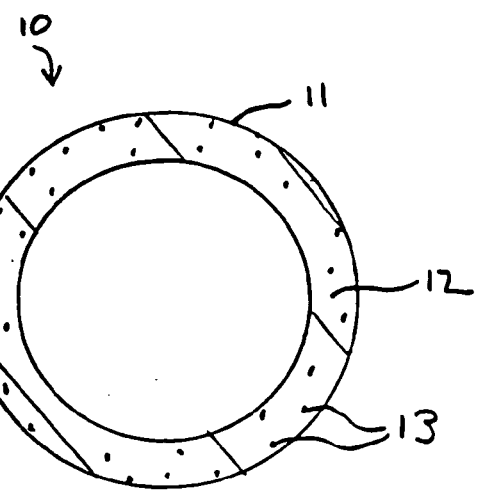
FIG. 10 illustrates a transverse cross-sectional view of a catheter which embodies features of the invention, having a catheter shaft formed of a polymeric matrix containing an oxidant producing component throughout the shaft.
Figure 11:
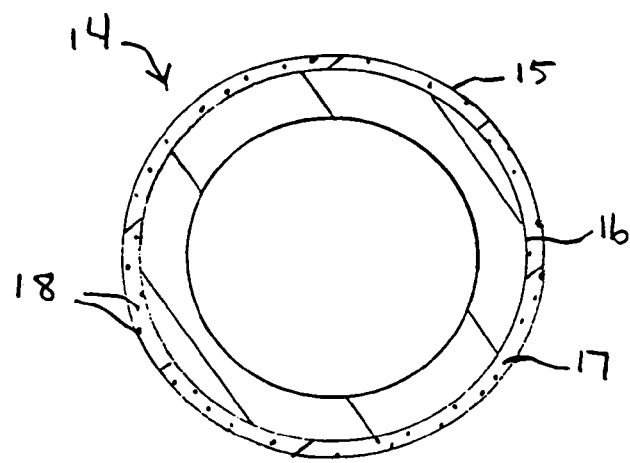
FIG. 11 illustrates a transverse cross-sectional view of a catheter which embodies features of the invention, having a catheter shaft having a body and a layer of a polymeric matrix containing an oxidant producing component in the polymeric matrix.

A variety of anti-infective medical devices may be provided in accordance with the invention, including catheters, guidewires, gloves, protheseses, implants, and contraceptive devices. A part of the medical device may be formed of the polymeric matrix containing an oxidant producing component throughout the part, or it may have a layer of the polymeric material containing an oxidant producing component. FIG. 10 illustrates a transverse cross-sectional view of a catheter 10 having a catheter shaft 11 formed of a polymeric matrix 12 containing an oxidant producing component 13 throughout the shaft. FIG. 11 illustrates a transverse cross-sectional view of a catheter 14 having a catheter shaft 15 having a body 16 and a layer of a polymeric matrix 17 containing an oxidant producing component 18 in the polymeric matrix. In the embodiment illustrated in FIG. 11, the layer 17 is on an outer surface of the catheter. However, it should be obvious that the layer may be on an inner surface of the body 18 or between inner and outer layers of the device. Although not shown, the polymeric matrix may contain one or more of an oxidizing agent, a reducing agent, and a proton source, depending on the nature of the oxidant producing component.

Figure 12:
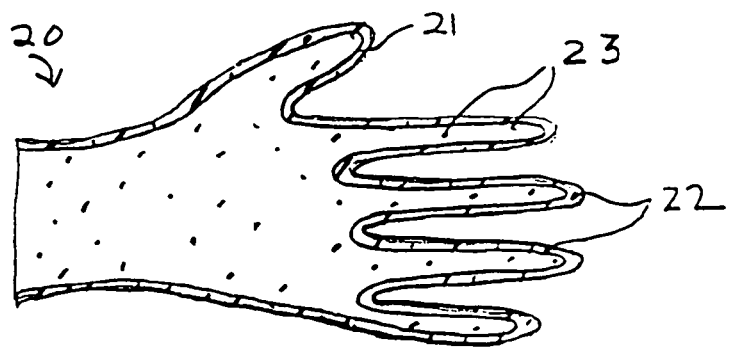
FIG. 12 illustrates a longitudinal cross-sectional view of a glove which embodies features of the invention, formed of a polymeric matrix containing an oxidant producing component and having a proton source dusted onto an inner surface of the glove.

One embodiment of the invention comprises a self-sterilizing glove. The self-sterilizing gloves may be formed by casting the polymer base over a suitable mold to form left- and right-handed gloves wherein at least one layer, preferably the last layer, containing the anti-infective component, contains all but a body fluid, the latter provided with solvation of the reactants by sweat, or other body fluids entering a ruptured glove exposed to body fluids, and wetting the inner surface of the glove coated with anti-infective reactants. Removal of the molded glove from its casting form with inversion of the glove presents the anti-infective coated polymer in close proximity to the skin where activation provides an anti-infective barrier to the wearer of the glove. The preferred embodiment involves leaving the exterior side of the glove free of anti-infective encapsulated reactants with only a thin skin of encapsulated anti-infective reactants coated on the side of the glove presented against the skin of the hand. A variety of suitable polymeric materials may be used including polyvinyl chloride, latex, polyurethane, or other suitable hydrophobic polymer commonly used in the manufacture of gloves. In the embodiment in which the polymeric material is typically processes in aqueous solutions, the polymeric matrix preferably does not contain one or more reactants required for reacting with the oxidant producing component to form the oxidant. For example, one or more of an oxidizing agent, reducing agent, or proton source may be provided as a separate layer. In one embodiment, a proton source is provided as a layer dusted onto a surface of the glove. FIG. 12 illustrates a longitudinal cross-sectional view of a glove 20 formed of a polymeric matrix 21 containing an oxidant producing component 22 and having a proton source 23 dusted onto an inner surface of the glove.

An example of the embodiment is as follows: using latex rubber, paint over a suitable mold, or dip the mold into the latex polymer, and air dry the latex to allow for the build up from three two six layers of latex coating as a polymer skin coating the mold. Thereafter, paint over the outer latex skin a mixture of 2% by weight sodium iodide, 8% sodium iodate, ground up as a fine powder of less than or equal to about 200 microns and suspended in latex polymer, and an additional two to three layers of iodide-iodate loaded latex allowing for the encapsulation of precursors for the formation of elemental iodine within the final layers of latex coating the mold. Upon drying, lightly dust the inverted glove with B.F. Goodrich Carbopol 971, 974, Polycarbopol, finely ground salts of sodium or potassium dihydrogen phosphate, finely ground pectin, or any other suitable proton source conferring to the glove's surface, when wetted, a pH of approximately 3.0 to 6.0, which allows for the formation of anti-infective elemental iodine upon wetting of the glove concomitant with solvation of encapsulated iodide and iodate. The iodide and iodate may each be varied in the polymer base from a weight percent relative to the polymer of from 0.05% to 10% by weight as desired to achieve varying free levels of iodine formation concomitant with wetting of the glove (providing a source of proton is also made available). In the absence of a proton source, no elemental iodine is detectable even with wetting of the surface encapsulated with iodide and iodate. Formation of elemental iodine is evident by the presence of a yellow hue to the inner surface of the glove with wetting of its inner surface. The preferred concentration of elemental iodine necessary to confer to the glove anti-infective properties ranges from about 2 to 100 ppm.

As mentioned above, the medical device of the invention may produce a variety of suitable anti-infective oxidants other than elemental iodine, including hydrogen peroxide, nitric oxide, hydroxyl radical, hypohalites, haloamines, thiocyanogen, and hypothiocyanite. The concentration of all solid powdered anti-infective precursors encapsulated within the polymer base should be in the range from about 0.01% to about 16% by weight relative to the polymer mass. Enzyme activity dispersed within, or attached to the surface, of the polymer, should range from no less than about 50 units to an upper range of about 330,000 units per gram solid. The preferred concentration range of halides egressing from the polymer base upon solvation should preferably range from about 1 mM to no more than about 200 mM. The concentration of thiocyanate egressing from the polymer, if encapsulated within the polymer base, should not be less than about 1 micromolar nor exceed about 5 millimolar.

The precursors of the oxidants are contained as solids into a hydrophobic polymer base as discussed above. The hydrogen peroxide generators include nonenzymatic reactants and enzymatic reactants. The nonenzymatic reactants include percarbamide, perborates such as alkali metal perborates such as sodium perborate monohydrate, sodium perborate tetrahydrate, sodium ubiquitous presence of chloride ions in solution wherein chloride ion and $H_2O_2$ serve as substrates of myeloperoxidase in forming hypochlorite. Alternatively, hypoiodite, or hypobromite, both of which also exhibit strong anti-infective activities, may be formed with inclusion of the alkali salts of iodine and bromine, respectively, encapsulated as dry powders within the polymer base.

Haloamines can be generated by encapsulation of hypohalite generators in the base polymer in combination with primary or secondary amines such as taurine, histidine, spermine, lysine, glycine and similar aliphatic and cyclic primary and secondary amines which upon exposure to hypohalites form the corresponding long-lived haloamines such as taurine chloramine, histidine chloramine, spermine chloramine, and the like.

Thiocyanogens and hypothiocyanites can be generated by encapsulation of the above $H_2O_2$ generators within the polymer base in combination with myeloperoxidase (donor: hydrogen-peroxide oxidoreductase; EC 1.11.1.7), lactoperoxidase (donor:hydrogen-peroxide oxidoreductase; EC 1.11.1.7), horseradish peroxidase (donor:hydrogen-peroxide oxidoreductase; EC 1.11.1.7), or other donor:hydrogen peroxide oxidoreductase, encapsulated within or attached covalently or noncovalently to the polymer surface, and a dry powder alkali salt of thiocyanate, wherein $H_2O_2$ and thiocyanate serve as substrates of the peroxidase in the formation of thiocyanogen, or its hydrolysis product, hypothiocyanite, in fluid coming into contact with the polymer upon solvation and egress of the encapsulated reactants.

Immobilization of Enzymes by Covalent or Noncovalent Methods to the Polymer Surface In the embodiments having enzymatic reactants, the enzymes can be attached to the polymeric material using conventional methods. For example, methods for the covalent and noncovalent attachment of enzymes to silicone and other hydrophilic and hydrophobic polymers include diazotization, amide bond formation, alkylation and arylation, amidation as well as ionic charge associations and hydrophobic binding as described in detail in:

Miller, R. E. (1972) Attachment of Enzymes to Siliceous Materials, U.S. Pat. No. 3,669,841.

Zaborsky, O. R. (1974) in, *Immobilized Enzymes*, CRC Publishing, Cleveland, Ohio.

Avrameas, S. et al. (1990) Immobilization of Active Protein by Cross-Linking to Inactive Protein. U.S. Pat. No. 4,970, 156.

Okamura, S. et al. (1976) Method for Manufacturing Medical Articles Composed of Silicone Rubber Coated with Collagen. U.S. Pat. No. 3,955,012.

Rohrback, R. P. et al. (1980) Support Matrices for Immobilized Enzymes. U.S. Pat. No. 4,206,259.

Hearn, M. T. (1987) 1,1'-Carbonyldiimidazole-Mediated Immobilization of Enzymes and Affinity Ligands. Meth. Enzymol. 135, 102–117.

Miron, T. and Wilchek, M. (1987) Immobilization of Proteins and Ligands Using Chlorocarbonates. Meth. Enzymol. 135, 84–90, incorporated by reference in their entireties.

Wetting of the polymer containing the encapsulated reactants during attachment of the enzyme to the surface of the polymer is not critical, nor does it defeat the performance of the polymer in releasing anti-infective activity. The period required for covalent and/or noncovalent attachment of the enzyme catalyst is of a brief duration, generally over a period of a few hours, wherein the solvation of encapsulated reactants is minimal relative to the reservoir of reactants retained within the polymer. Furthermore, by judicious choice of the attachment method the pH, oxygen tension, or other critical substrate, can be manipulated to preclude formation of reactive products during enzyme attachment. In the case of donor:oxygen oxidoreductases (for example, glucose oxidase (D-glucose:oxygen 1-oxidoreductase; EC 1.1.3.4)), attachment of the enzyme under anaerobic conditions using aqueous solutions purged of oxygen deprives the enzyme of oxygen as a co-substrate in the formation of hydrogen peroxide, and therefore prevents premature formation of anti-infective products. Similarly, the exclusion of a halide source while coupling myeloperoxidase precludes formation of a hypohalite during the immobilization of myeloperoxidase to the surface of the polymer base. Upon completion of the enzyme immobilization step, the polymer can be dried by air, or by blotting on a suitable absorbent such as paper or felt, so that the residual moisture left on the surface precludes any further solvation of encapsulated reactants.

In certain instances where the chemistry precludes attachment of the enzyme to the surface of the polymer directly because of too rapid of release of reactants from the polymer during the attachment phase, and where entrapment of enzyme within the polymer base is deemed too costly or inefficient, the enzyme can instead be immobilized to a second, thin polymer film lacking reactants. The latter film containing immobilized enzyme can be attached to the implant polymer containing encapsulated reactants in the form of an elastic band, grid, or patch, bringing the enzyme in close proximity to the surface of the polymer containing encapsulated reactants. In this manner the enzyme serves to catalyze reactants into anti-infective products as the reactants solvate and egress to the surface of the implanted polymer.

EXAMPLE 1

This example illustrates the incorporation of iodide into a silicone disc device and long term release rates of iodide upon submersion and washing of the device in buffer. Finely ground sodium iodide (3 g), prepared in a mortar and pestle, was mixed into 10 g of RTV silicone elastomer (polydimethylsiloxane) to which was also added 1 g dibutyl tin dilaurate catalyst stock solution. The ground crystalline sodium iodide powder recovered from the mortar and pestle was added last to the polymer base after thorough mixing of the catalyst into the silicone, and the silicone then poured into 5.0 cm diameter Petri dishes to a depth of 0.3 cm in thickness. After 24 hrs, the cured disc was removed, thoroughly rinsed in 10 mM sodium phosphate buffer, pH 5.6, made up in 150 mM NaCl, and then placed into a 150 ml beaker containing 10 ml of the same buffer. At varying intervals (see FIG. 1), including an initial t=0 measurement, buffer was drained from the beaker and device, and set aside for analysis of iodide content. The release of iodide was measured after mixing $H_2O_2$ (~56 mM) with 1 ml aliquots of the sample washings. The assay tracked formation of elemental iodine at 350 nm in a Shimadzu UV-265 double beam spectrometer against a standard calibration curve constructed with known quantities of sodium iodide made up in the same buffer and worked up in the same manner. Fresh 10 ml aliquots of buffer were washed over the device for analysis of subsequent release of iodide over the next interval, and this process was repeated over a period of approximately 30 days. In between, the device immersed in buffer was left on a shaking rocker platform at room temperature. Precautions were taken to minimize evaporation between sampling intervals by covering the top of the beaker with plastic wrap.

FIG. 1 shows that sodium iodide, incorporated at a ratio of solid to elastomer of ~30% into the polymer base of the fabricated device, allowed for the release of iodide (upon immersion and sequential changes in buffer). The peak iodide release was at around 50 to 60 mM (in a fluid volume of 10 ml buffer per washing interval). The capacity of the device to restore iodide to this level with sequential changes in buffer remained relatively constant over the first 350 hrs, and then declined to ~20 mM by around 600 hrs of continuous immersion and rinsing of the device in buffer. Calculations of iodide recovery, relative to the iodide initially available in the device, indicated that by 600 hrs of continuous immersion and washing under the above conditions ~90% of the iodide was leached from the device.

EXAMPLE 2

This example illustrates the release of glucose oxidase and horseradish peroxidase encapsulated within a device fabricated from a silicon elastomer. Specifically, the device was fabricated with a glucose oxidase/horseradish peroxidase and iodide formulation into a disc with silicone elastomer. The subsequent release of the formulation from the device was measured after immersion and continuous bathing in buffer. RTV Silicone elastomer (10 g, polydimethyl siloxane with silanol end caps) was mixed with silicic ester dibutyl tin dilaurate catalyst (1.1 g), and into this uniform mixture 50 mg crystalline glucose oxidase (D-glucose:oxygen 1-oxidoreductase; EC 1.1.3.4), 5 mg crystalline horseradish peroxidase (donor:hydrogen-peroxide oxidoreductase; EC 1.11.1.7) and 3 g of finely ground sodium iodide were slurried. The slurry was poured into 5.0 cm diameter Petri dish to a thickness of ~0.1 cm, cured for approximately 24 hours at room temperature, removed from the mold, briefly rinsed in distilled water, placed in a 150 ml beaker, wetted with 1 ml of sodium phosphate (10 mM), pH 5.6, also containing 150 mM NaCl, then left on a continuous rocker platform. This allowed for the buffer fluid to continuously wash across the device's surface. At timed intervals, buffer was drained from the beaker and replaced with an equivalent volume of fresh buffer. Between intervals the beaker was kept tightly covered to prevent evaporation.

To evaluate egress of glucose oxidase and horseradish peroxidase generating activities from the fabricated device, wash buffer (200 μl), in which the device was immersed, was mixed with an equal volume of 10 mM sodium phosphate, pH 5.6, made up in 100 mM potassium iodide and 100 mg/dl glucose. With glucose and iodide additions to the test washings there was observed a rapid development of yellow coloration in the assay mixture. The yellow coloration was confirmed by spectral scans on a Shimadzu UV-265 double beam spectrometer to be characteristic of $I_3^-$ formation (e.g., complexation of elemental iodine with iodide), indicating the release of glucose oxidase and horseradish peroxidase from the device. This conclusion, that glucose oxidase and horseradish peroxidase were egressing from the device and at levels sufficient to catalyze formation of nascent elemental iodine, was further confirmed through a spot test for glucose oxidase. Hence, omission of glucose resulted in no color formation.

The formation of elemental iodine was also confirmed by extracting an aliquot of the yellow colored assay solution with chloroform and observing elemental iodine in the chloroform layer. The lower chloroform layer took on a characteristic pink-violet color typical of elemental iodine (absorbance max, 508 nm). Horseradish peroxidase was also confirmed to be egressing from the disc by conducting a separate spot test for peroxidase activity using o-dianisidine as substrate in place of iodide. This latter substrate did not show the propensity to oxidize readily in the presence of $H_2O_2$. However, peroxidation of o-dianisidine was evident upon replacing iodide with o-dianisidine substrate in the standard assay. Furthermore, control tests run with glucose oxidase alone showed that the formation of triiodide (e.g., yellow coloration) was delayed well beyond 30 seconds under the experimental conditions employed, all of which therefore confirmed the egress of both glucose oxidase and horseradish peroxidase from fabricated device immersed in wash buffer.

A 30 second test for visual detection of elemental iodine formation in the form of $I_3^-$ was used to semi-quantitatively track the device's reservoir capacity in releasing glucose oxidase and horseradish peroxidase to the wash buffer with repeated submersion and washing. Table 1 summarizes the results of these experiments.

TABLE 1

Diffusion of GO and HPO from Silicone Device into Immersion Buffer v. Washing Interval

| Sampling Interval Post Immersion of Disc (hrs) | GO/HPO Released into Buffer Washing? | Comments |
| --- | --- | --- |
| 0 | – | test on wash buffer at t = 0. |
| 4.5 | + | very strong (<30 sec) |
| 29.0 | + | " |
| 50.8 | + | " |
| 75.8 | + | " |
| 97.8 | +/– | weak response; color in 30–60 sec |
| 125 | +/– | weak response; color in 30–60 sec |
| 153 | +/– | weak response; color in 30–60 sec |
| 174 | +/– – | Very weak; color >60 sec |
| 196 | +/– – – | Very weak; color >120 sec |

At the sampling intervals indicated, buffer (10 mM sodium phosphate, pH 5.6, made up in 150 mM NaCl) was removed for testing and replaced by a fresh 1 ml aliquot. Controls (exclusion of glucose from test mixture) tested negative for yellow coloration (triiodide). These data show that a significant release of glucose oxidase and horseradish peroxidase from the device occurred under the conditions in which it was fabricated and tested over a period of approximately 4–5 days. These data further show that residual iodine activity continued to egress from the device, albeit at lesser levels, over a period up to 8 to 9 days duration.

EXAMPLE 3

This example illustrates iodate reduction and conversion to elemental iodine and microbicidal tests on fabricated devices encapsulated with iodate and iodide in silicone-based polymer. Based upon evidence that many body fluids are rich in reducing compounds, antioxidants, and the like, alternate methods of generating elemental iodine de novo from iodide and iodate were investigated using Brain Heart Infusion (BHI) media to mimic complex body fluid conditions. BHI is a rich source of reducing compounds of the type found in body fluids. The formation of elemental iodine de novo from iodide and iodate in BHI media was confirmed by titrating solutions of BHI with incremental additions of iodide and iodine pentoxide (the anhydride of iodate), either in combination, or with iodine pentoxide alone. Following additions of trace amounts of iodide in combination with iodine pentoxide (total iodine<1 mg/ml broth media), the BHI media took on an intense yellow-orange hue, indicative of $I_3^-$ formation (e.g., formation of elemental iodine and its complexation with iodide ion). The presence of elemental iodine was confirmed by extraction of BHI media titrated in this manner with chloroform, which revealed the characteristic intense violet color of elemental iodine associated with its partitioning into the lower chloroform layer (absorbance max, 508 nm). These data were interpreted as evidence of robust elemental iodine production arising by the reductive conversion of iodate to elemental iodine, but also as evidence that iodate was oxidizing added iodide into elemental iodine in accordance with theoretical expectations based upon the chemistry of iodate.

This latter conclusion was based upon the observation that addition of iodate (in the form of iodine pentoxide) alone to BHI media did not alter the coloration to the media. Further additions in excess of 1 mg/ml, however, ultimately led to a similar set of findings to those seen with additions of iodide and iodate to the broth media. These results were interpreted as evidence of conversion of iodine pentoxide to iodate, reduction of iodate to iodide by reducing equivalents present in BHI, and subsequent oxidation of iodide to elemental iodine by further additions of iodine pentoxide to the media. The interconversions appeared complex and dependent upon the rate of reduction of elemental iodine and iodate to iodide by reducing equivalents in the media, as opposed to the opposing rates of oxidation of iodide to elemental iodine caused by the presence of iodate in the broth media and the rate at which iodine pentoxide spontaneously hydrolyzes to iodate.

Disc shaped silicone devices were prepared as in example 1, except formulations of iodide and iodine pentoxide, or iodine pentoxide alone and in combination with NaCl as a carrier were incorporated into the silicone. The formulations were aimed at testing the device's capacity to produce microbicidal activity upon submersion in BHI broth media. Specifically, sodium iodide (3 g) was ground to a fine powder under anhydrous conditions with iodine pentoxide (1 g) and dispersed in 10 g of silicone elastomer premixed with silicic ester dibutyl tin dilaurate catalyst, then poured into 50 mm Petri dishes and processed as in Example 1. Smaller discs were cut from the device using a hole punching tool in producing silicone tablets of 6 mm diameter. These were placed in BHI media, previously adjusted to pH 4.0, at 1 tablet per ml, and the BHI media containing the tablets then inoculated with test organisms, as noted in Table 2 (below).

A similar device was prepared using NaCl in place of sodium iodide at 2 g per 10 g of silicone polymer base. Tablets from this device were also tested for microbicidal activity upon introduction to inoculated BHI media as described in Table 3 (below). As expected, all of the tablets formulated with both iodide and iodine pentoxide produced an intense yellow coloration immediately upon contact with BHI media, indicative of instantaneous elemental iodine formation. Tablets with only iodine pentoxide present had no discernible effect on the coloration of the BHI media.

TAB3LE 2

Microbicidal Activity of iodide/iodate Encapsulated Silicone Tablets - Recovered CFU/ml Following Inoculation in BHI Media and Saline.

| | Inoculation | Inoculation Medium | |
| --- | --- | --- | --- |
| Organism | Time (hrs) | Saline | BHI, pH 4.0 |
| C. albicans | 0 | 66000 | 40000 |
| | 24 | <10 | <1000 |
| | 48 | nd | <10 |
| L. casei | 0 | 500000 | 500000 |
| | 24 | <10 | <1000 |
| | 48 | nd | <10 |

Incubations conducted at 35° C.
nd = not determined.

TABLE 3

Microbicidal Activity of iodine pentoxide Encapsulated Silicone Tablets - Recovered CFU/ml Following Inoculation of Test Media.

| Organism | Inoculation Time (hrs) | Inoculation Medium | |
|---|---|---|---|
| | | Saline | BHI, pH 4.0 |
| C. albicans | 0 | 140000 | 100000 |
| | 3.5 | <10 | <1000 |
| | 22 | <10[a] | <10[b] |

Incubations conducted at 35° C.
nd = not determined.
[a]chloroform extraction on residual culture media - no appearance of violet coloration.
[b]chloroform extraction on residual culture media - strong violet coloration indicative of elemental iodine presence.

FIG. 2 also shows the kinetic release of iodine pentoxide from discs prepared in the same manner as in the microbicidal studies summarized in Table 3. The discs were suspended in 100 mM sodium citrate, pH 4.0, at 1 tablet per ml, but using different mass concentrations relative to the polymer base used in fabricating the silicone device. The concentration of iodate released was proportional to the mass encapsulated into the polymer (FIG. 2). In these experiments the total salt (NaCl) mixed into the silicone polymer was held constant at 30% and comprising iodine pentoxide and NaCl as necessary to maintain a constant salt:polymer ratio, but at concentrations of iodine pentoxide per unit polymer mass of 2% and 10%, respectively. Complex media, such as BHI, had no discernable impact on the solvation and diffusion rates of iodine pentoxide as similar rates of iodine pentoxide release were seen substituting BHI media in place of citrate buffer.

The data from Tables 2 and 3 show that elemental iodine mediated killing of the microorganisms tested. These data were generated as a result of fabricating the device with varying concentrations of iodide in combination with iodine pentoxide and placing tablet samples from the device within the BHI media rich in reducing compounds, or saline. The organisms supplied their own source of reducing compounds to the device tablets. The levels of iodate required for effective microbicidal activity appeared to be <<5 mM, based upon measurements of iodate released from the tablets, and by an examination of the killing interval after introduction of the tablets to inoculated cultures (see, for example, Tables 2 and 3, and FIG. 2). For example, the data in Table 3 indicates effective killing occurred within 3 to 4 hours of exposure to the iodine pentoxide tablets. Assuming all of the iodate released into the media could be converted to elemental iodine, this suggests an upper limit of iodine in the BHI media could not theoretically exceed ~125 mg/dl (e.g., 5 mM elemental iodine). The elemental iodine concentration was found experimentally to be far less than this calculation (see below). Chloroform extracts made on the cultured BHI media in which iodate was found to be present also showed no evidence of significant elemental iodine accumulating (i.e., no coloration of the chloroform layer occurred) affirming that little actual elemental iodine accumulated in the broth medium. Without being bound by theory, these latter observations indicate that elemental iodine killing likely and predominantly occurred at the microbe's cell wall (Tables 2 and 3), and possibly through release of reducing compounds on the microbe's cell surface. This would cause de novo formation and uptake of elemental iodine into the lipid bilayer of the microbial cell membrane.

These data indicate that elemental iodine concentrations required to affect microbial killing are generally <<0.01% (that is, as much as two orders of magnitude below the iodine content of povidone-iodine solutions). The lower elemental iodine concentrations required and produced by the inventive device, relative to iodophor vehicles such as povidone-iodine, are attributed to the fact that iodate was released slowly over a period of time using the fabricated silicone device as the vehicle for its presentation in solution. Further, recycling of iodate to iodide, and then back to elemental iodine, likely occurred continuously as fresh iodate continued to egress from the device and encounter reducing compounds, and iodide recycled from elemental iodine formed in an earlier cycle, in its path. Thus, even trace quantities of iodide can be envisioned to recycle in the reaction media until taken up by the microbial cell in the form of elemental iodine, whereupon killing of the microbe then ensues.

EXAMPLE 4

This example illustrates the microbicidal activity and optimization of iodate and iodide formulations for de novo formation of elemental iodine. Experiments were performed to optimize formulations used in fabricating the inventive device formulated with silicone elastomer. Finely ground iodate and iodide were mixed into silicone elastomer in various loadings relative to the elastomer. The polymer was allowed to cure with dibutyl tin dilaurate catalyst additions, and then devices were prepared (0.6 cm diameter 0.3 mm thick) using "hole punch" tablets from the disc shaped device to test for microbicidal activity using C. albicans inoculated BHI. BHI media was adjusted to pH 4.0 with HCl, and an inoculum of approximately $1 \times 10^5$ CFU/ml C. albicans (ATCC 66027) was added to the broth media. Tablets obtained from the fabricated device were suspended in the inoculum at 1 tablet/ml. At varying intervals, aliquots of the inoculum, incubated at 35° C. in air, were subcultured to sheep blood agar plates and incubated for an additional 24 hours at 35° C. in air to determine the effect of the varying formulations on the C. albicans inoculums.

Tablets obtained from devices formulated in the range of 1% to 16% by weight iodide alone relative to silicone elastomer (total salt, 30% by weight with the difference made up with NaCl as a carrier salt) showed no microbicidal activity. Tablets made up in the same manner, but with iodate alone ranging from 0.5 to 12% by weight, showed no microbicidal activity against C. albicans at 24 hours exposure. However, in the range of 4 to 12% iodate a 1 to 2 log decrease in growth at 48 hours exposure, and <10 CFU/ml were found with 72 hours exposure.

Tablets obtained from silicone devices made up with varying weights of iodate ranging from 2 to 4% by weight, and iodide ranging from 0.1 to 0.25% by weight combinations (additional weights of NaCl added to bring the final salt weight relative to silicone to 30%), showed no microbicidal activity. However, with increasing weights of iodide in excess of 0.5% by weight in the presence of 4% by weight or greater iodate, complete killing of C. albicans occurred within 24 hours of submersion of the tablets within the BHI inoculums. Therefore, the lower limit of the formulation needed to effect killing within 24 hours exposure in complex BHI media amounted to approximately 4% iodate, 0.5% iodide and 24.5% NaCl salt (ground to <200 microns) all by weight suspended in the silicone base used in fabricating the devices. Further tests revealed that formulations varying from 4% to 8% iodate, and from 2% to 16% iodide all by weight were very efficient in killing *C. albicans* with complete killing occurring in less than 4 hours of submersion of the silicone tablets within the BHI inoculums.

PVP was also found to improve the stability of the silicone formulation by acting as both a desiccant and an iodophor, such as by preventing moisture from the atmosphere from prematurely activating the iodide salts mixed into the silicone elastomer. By inclusion of from about 1% to about 10% finely ground PVP by weight together with iodate and iodide in fabricating the microbicidal disc shaped device, the final device obtained after curing of the elastomer showed less tendency to express elemental iodine upon exposure to air over time. No adverse effects of including PVP in the salt formulations were observed with regard to alteration of the device's microbicidal activity. The optimal iodide salt formulation based upon the tablet tests used was 8% iodate, 2% iodide and 10% PVP with omission of NaCl from the final salt mixtures. The latter "carrier" salt was found to provide no obvious benefits in fabricating the device, nor did it appear to have any significant effect on the release rates of the salt formulations encapsulated within the silicone device.

Concomitant with the microbicidal killing studies, measurements were made on the release of iodate, iodide and formation of elemental iodine during submersion of the tablets in citrate buffered solutions. The release rates were experimentally indistinguishable whether tablets representing the device embodiment were submerged in BHI or 100 mM Citrate buffer, pH 4.0, whereas reducing compounds present in BHI consumed some of the elemental iodine as it was formed when the tablets were immersed in the latter media. For this reason, the chemical profile for release of the iodide and iodate, and elemental iodine formed, was tracked in citrate buffer. FIG. 3 shows the release of iodate, and iodide, from submerged tablets (1 tablet/ml in citrate buffer) incubated at room temperature over a period of approximately 32 hours. In these experiments, iodate was tracked by drawing 20 µl aliquots of the test solutions which were subsequently allowed to oxidize iodide to elemental iodine in the presence of excess iodide, and by which the formation of $I_3^-$ was then quantitated spectrally at 350 nm in a standardized assay. A calibration curve using the same assay was constructed with known concentrations of iodate from which the concentration of iodate released from the tablets was determined as a function of submersion interval (see FIG. 4). Iodide was tracked by obtaining 200 µl aliquots and oxidizing the iodide to elemental iodine in the presence of excess iodate, and extracting the latter into chloroform for spectral quantitation at 508 nm against a calibration curve constructed under identical assay conditions, but with known concentrations of iodide. The results of these chemical tracking experiments, matched with the microbicidal killing studies, and revealed that a critical media concentration of iodate in the range of 1 to 2 mM, and iodide concentration of from 0.5 mM or higher, was necessary to effect *C. albicans* killing. Tablet formulations, which failed to kill *C. albicans* within the first 24 hours, or less, failed to do so because the threshold levels of iodate and iodide were not achieved.

FIG. 4 shows the accumulation of elemental iodine in the citrate buffer tracked over a longer period of approximately five days submersion of the iodate/iodide/PVP loaded tablets (1 tablet/ml). Each point represents an experiment in which three tablets in 3 ml 100 mM citrate, pH 4.0, were submerged for the interval shown, and then an aliquot (1 ml) of the buffer solution assayed for residual elemental iodine. Elemental iodine was quantitated by extracting citrate buffer aliquots in chloroform (1 ml), and reading the absorbance at 508 nm against a calibration curve constructed with crystalline elemental iodine made up in chloroform at known concentrations expressed in ppm elemental iodine. While there was significant variability in the generation of free elemental iodine over the five day interval examined, elemental iodine ranged from a low of approximately 2 ppm to a high of 70 ppm in this series of experiments. The maximum elemental iodine level peaked around 36 to 48 hours after submersion of the tablets in citrate buffer.

EXAMPLE 5

This example illustrates the fabrication of a hydrogel device embodiment that is activated upon contact with aqueous fluids. Two percent "medium viscosity" sodium alginate was mixed with an equal volume of 2% Carbopol 971 (B.F. Goodrich) (cross-linked polyacrylate) to yield a composite 1% viscous gel solution, pH 3.95, made up in equivalent weights of alginate and Carbopol. This gel mixture was chilled to ~4° C. 100 mM potassium iodide made up in water was then mixed thoroughly into the gel to yield a final concentration of 1 mM potassium iodide. An equivalent amount of 100 mM sodium iodate was rapidly mixed into the gel to yield a gel mixture comprised of 1 mM sodium iodate, 1 mM potassium iodide, 1% alginate and 1% Carbopol 971. This mixture was quickly frozen at −70° C., lyophilized overnight under vacuum, and yielded a fine, highly porous, lightweight, sponge-like product, red-brown in appearance. The sponge-like product was cut into various shapes and left in sealed containers (to keep out moisture) at room temperature without loss of its nascent elemental iodine generating capacity (that is, upon solvation in aqueous solutions).

Upon addition of water to the sponge-like material, its color changed almost instantly from red-brown to an intense canary-yellow, revealing rapid formation of nascent elemental iodine complexed to iodide in the form of $I_3^-$, and it thickened into a viscous hydrogel. The presence of nascent elemental iodine was confirmed by extraction in chloroform and verification by spectral scanning of the final extract (e.g., absorbance max, 508 nm; product lost upon addition of excess reducing agents to the rehydrated gel). Various shapes of the sponge-like product were also prepared by freezing gel mixtures immediately after addition of iodate and iodide, and before significant elemental iodine was allowed to form.

While the rate of elemental iodine formation in the same gel mixtures was very much slower when first prepared in aqueous form for freezing, following freezing and lyophilization, iodate and iodide rapidly produced elemental iodine, as noted, within seconds of coming into contact with aqueous solutions. This was determined to be the result of the concentrating effect of lyophilization, such that solvation allowed for much higher concentrations of iodate and iodide to interact with one another in generating elemental iodine then was possible prior to the freezing and lyophilization. After lyophilization, in the absence of water, iodate and iodide were not free to interact with one another pending their solvation. Hence, this embodiment of the invention, referred to as the hydrogel device, allowed for incorporation of all of the essential reactants within a single matrix (e.g., the hydrogel polymer).

A hydrogel embodiment device was also prepared using glucose oxidase (D-glucose:oxygen 1-oxidoreductase; EC 1.1.3.4) (10 µg/ml) and horseradish peroxidase (donor: hydrogen-peroxide oxidoreductase; EC 1.11.1.7) (3 µg/ml)

mixed into a 1% alginate-Carbopol gel suspension made up in water at room temperature to which potassium iodide at a final concentration of 2 mM was added. The gel mixture was frozen and lyophilized as in the iodate/iodide embodiment. The sponge-like product (in this case) exhibited an off-white color with a tinge of yellow, and could be stored for several weeks at room temperature without loss of nascent elemental iodine generating activity triggered by the addition of glucose (~50 mg/dl). Controls in which water was added in place of glucose solution showed no elemental iodine formed. In both instances, the sponge-like product quickly solvated to a viscous, mucous-like hydrogel. Elemental iodine was confirmed by recovery of elemental iodine in chloroform extracts similar to hydrogel delivery devices formulated with iodide and iodate. The concentration of glucose used to activate the glucose oxidase/horseradish peroxidase formulated delivery device was not particularly critical in that solutions as low as 10 mg/dl and higher concentrations in the range of 100 mg/dl, when added to the desiccated gel, triggered nascent elemental iodine formation.

Both embodiments of hydrogel formulations cited in this example showed formation of nascent elemental iodine ranging from a low of a few ppm to an upper limit in the range of 100 ppm. The elemental iodine formation was commensurate with the concentrations of glucose oxidase/horseradish peroxidase, or iodide and iodate incorporated into the hydrogel prior to freezing and lyophilization of the gel mixtures. Elemental iodine was seen to persist in the thick gel mixtures for a period of approximately 8 to 10 hours after which it tapered off to undetectable levels.

FIG. 5 shows de novo formation of elemental iodine upon solvation of a lyophilized 1% "high viscosity" pH 4.0 alginate inventive device embodiment prepared in the form of a cylinder. The initial formulation comprised a 2 mM potassium iodide solution and a 2 mM sodium iodate solution. The gel was cast in 100 (length)×0.6 cm (internal diameter) tubes in the frozen state, lyophilized and cut longitudinally into 1 cm sections. Control gel was prepared in the same manner but with omission of iodide and iodate from the final mixtures. Elemental iodine was measured following 20 minutes submersion of the alginate formulation (1 cm lengths) in 1 ml 100 mM citrate buffer, pH 4.0. Values shown (FIG. 5) represent the average of triplicate experiments compared to control results using alginate formulated in the same manner except for the exclusion of iodide and iodate from the polymer matrix. Concomitant with the in situ formation of elemental iodine, the gel swelled to a viscous, mucous-like, hydrogel characteristic of its original composition prior to lyophilization.

EXAMPLE 6

This example illustrates the exploitation of proton ($H^+$) formation in driving the formation of nascent elemental iodine. On chemical grounds, the oxidation of iodide to elemental iodine requires $H^+$ as one of the reactants in driving the reaction to completion whether iodide is oxidized by $H_2O_2$ or by iodate. This can be fully appreciated in considering the stoichiometry of the oxidative reactions illustrated in equations 1 and 2 below:

$$2H^+ + 2I^- + H_2O_2 \rightarrow I_2 + 2H_2O \quad \text{Equation 1}$$

$$6H^+ + 5I^- + IO_3^- \rightarrow 3I_2 + 3H_2O \quad \text{Equation 2}$$

It follows that elemental iodine generating formulations designed to enhance $H^+$ production should facilitate nascent elemental iodine formation in providing $H^+$ required in converting iodide into elemental iodine de novo.

Two embodiments were used to demonstrate this principle: one involving $H^+$ formation through the action of glucose oxidase (D-glucose:oxygen 1-oxidoreductase; EC 1.1.3.4) on glucose catalyzing concomitant formation of $H_2O_2$ and gluconic acid; the other involving spontaneous hydrolysis of the iodine pentoxide resulting in the concomitant formation of iodate and $H^+$ (the ionized product of iodic acid). $H^+$ generators or donors that allow for this phenomenon are not limited to these two compounds. They can include any one or a number of synthetic polyanhydrides, polycarboxylic compounds, and the like (such as, polylactides, polygalactides, acetic anhydrides, etc.).

In one formulation, iodine pentoxide was encapsulated within a silicone device, prepared as in example 2, but in combination with iodide at a mass ratio of 2% iodide and 4% iodine pentoxide substituted in place of iodate. A similar device was fabricated using 8% by mass iodate in place of iodine pentoxide. Upon curing the two devices, "hole" punch tablets of each cut at approximately 0.6 cm in diameter and 0.3 cm thickness were submerged at 1 tablet per ml in a total volume of 5 ml 100 mM sodium citrate, pH 4.0. The rate of elemental iodine formation was tracked visually in the buffer medium by observing the rate of $I_3^-$ egressing from each tablet. Chloroform extraction of the buffer medium was also used to visually confirm the formation of elemental iodine (evident in the violet extract recovered in the chloroform layer).

Tablets obtained from the device formulated with iodine pentoxide in place of iodate showed more than twice the rate of elemental iodine formed relative to tablets obtained from device fabricated with iodate. These data are consistent with the notion of solvation of iodine pentoxide as an anhydride and its subsequent rapid hydrolysis to $HIO_3$ (which can occur with solvation of iodine pentoxide). Therefore, there was simultaneous production of $H^+$ and iodate. The faster rates of elemental iodine formation seen in the tablets containing iodine pentoxide were attributable to $H^+$ formation. This conclusion was based upon the observation that the actual available amount of iodate was equivalent in both devices (e.g., 4% iodine pentoxide is the equivalent of 8% iodate based upon the stoichiometry that two moles of iodate and two moles of $H^+$ are released for every mole of iodine pentoxide solvated), and in consideration of equation 2. These results further indicate that the formation of elemental iodine was limited by the available supply of $H^+$ in solution and validated by fabricating devices formulated with iodate and iodide as above, but also including 10% citric acid in the formulation. In the citric acid embodiment, the rate of elemental iodine formation exceeded even that seen with devices fabricated with iodine pentoxide formulations. These data support a notion of an abundance of excess $H^+$ solvating via citric acid encapsulation within the device.

The utility of using $H^+$ production to drive more efficient production of nascent elemental iodine was further investigated in the second embodiment. Specifically, test solutions using glucose oxidase (D-glucose:oxygen 1-oxidoreductase; EC 1.1.3.4) and glucose in combination with horseradish peroxidase (donor:hydrogen-peroxide oxidoreductase; EC 1.11.1.7) and iodide were prepared. The rates of nascent elemental iodine released were tracked spectrally at pH 4.5 versus pH 7.4. This pH difference was chosen because earlier measurements of rates of nascent elemental iodine formation in the presence of 1 mM $H_2O_2$, or less, showed that the rate of elemental iodine formation was several orders of magnitude slower at pH 7.4 compared to pH 4.5.

The pH observation used $H_2O_2$ alone mixed with iodide. However, the latter reaction involved the consumption of one mole equivalent of molecular $O_2$ and $H_2O$ yielding $H_2O_2$ and gluconic acid. Gluconic acid, as a carboxylic acid like citric acid, is able to readily dissociate into its carboxylate anionic form, yielding gluconate, and providing one $H^+$ equivalent for every mole equivalent of $H_2O_2$ formed in the reaction. Therefore, $H^+$ can be generated to enhance elemental iodine formation in accordance with the reactions outlined in equation 1. This conclusion is supported by the above-noted data that tested rates of elemental iodine formation at the two pH ranges (pH 4.5 and pH 7.4) and used glucose and glucose oxidase (D-glucose:oxygen 1-oxidoreductase; EC 1.1.3.4) as a source for generating $H_2O_2$ oxidant concomitant with $H^+$ production in driving oxidation of iodide into elemental iodine. The latter rate measurements were compared with those seen without glucose oxidase as the driving reaction in generating $H_2O_2$.

FIG. 6 shows that glucose oxidase in combination with glucose accelerated elemental iodine formation through its capacity to provide $H^+$ at the same time it provided $H_2O_2$ oxidant for driving elemental iodine production via the peroxidative reaction outlined in equation 1. In these experiments, the rate of elemental iodine formation was investigated using a fixed concentration of iodide (50 mM) made up in 100 mM sodium citrate, pH 4.5, also containing 3 U/ml horseradish peroxidase and 100 mg/dl glucose, and in 10 mM sodium phosphate, pH 7.4, made up in 150 mM NaCl, 100 mg/dl glucose and 3 U/ml horseradish peroxidase, and variable levels of glucose oxidase as indicated. Rates of elemental iodine formation were tracked spectrally at 350 nm by measuring $I_3^-$ formation at 350 nm on a Shimadzu UV-265 double beam spectrometer. Kinetic rates were instantaneous upon addition of glucose oxidase to reaction mixtures, and linear in excess of 2 Absorbance units per min, and comparable whether allowed to occur at pH 4.5 or 7.4. The comparable rates indicate that the oxidation of iodide was driven by both $H^+$ and $H_2O_2$ production. $H^+$ was being consumed as quickly as it was formed in the enzymatic reaction. However, the formation of elemental iodine near neutral pH was primarily limited by available $H^+$ (e.g., there was a $H^+$ deficit).

The data in FIG. 6 show comparable rates of elemental iodine formation that occurred at pH 4.5 versus pH 7.4 and were driven through using glucose oxidase and glucose as the source of $H_2O_2$ and $H^+$ formation, allowing for peroxidation of iodide into elemental iodine. Moreover, the anhydride studies above, indicate that methods for introducing $H^+$ into formulations used in fabricating the inventive microbicidal devices improve the de novo rate of formation of elemental iodine. These data establish that preferred formulations exploit $H^+$ production by enzymatic mechanisms (e.g., glucose oxidase(D-glucose:oxygen 1-oxidoreductase; EC 1.1.3.4)), or incorporate anhydrides (which can serve to hydrolyze upon solvation and egress from the delivery device such as with iodine pentoxide), or incorporate polycarboxylic acid $H^+$ donors (e.g., alginic acid, Carbopol or citric acid). Polycarboxylic acid $H^+$ donors are capable of giving up $H^+$ to the oxidative reaction involving conversion of iodide into elemental iodine. Preferred $H^+$ driven formulations more efficiently drive chemical conversion of iodide into nascent elemental iodine.

EXAMPLE 7

This example illustrates the release of iodide and iodate and the formation of elemental iodine from cannular devices coated with silicone polymer containing elemental iodine generating iodide/iodate formulations. FIG. 7 shows the kinetic release of iodide and iodate upon submersion of silicone and polyethylene tubing coated on its external surface with a thin layer of silicone elastomer containing with 2% sodium iodide, 8% sodium iodate and 10% PVP prepared prior to curing, as in Example 4. Prior to curing the formulated silicone elastomer, silicone tubing of 1 cm outer diameter, and polyethylene tubing of approximately the same diameter, were each dipped in the formulated elastomer, and then allowed to cure overnight at room temperature. Sections of 2.5 and 5 cm lengths were cut from the precoated silicone and polyethylene cannulae, rinsed in distilled water, and then submerged in 5 ml of 100 mM sodium citrate pH 4.0. The kinetic release of iodide (dashed lines) and iodate (solid lines) (FIG. 7) from the coated tubing was measured. The thickness of the coating of the formulated polymer was not less than 0.08 mm nor greater than 0.15 mm.

FIG. 7 shows that using the above formulation, that iodate was released efficiently from the coated devices, peaking at between 2.5 mM and 4 mM around 24 hours after submersion in the buffer solution. Iodide was also recovered in the buffer wash, but at much lower concentrations, in the range of 0.1 to 1.0 mM depending upon the substratum to which the polymer formulation had been coated. Polyethylene yielded somewhat lower recoveries than silicone as the substratum to which the polymer formulation had been coated (silicone, filled squares; polyethylene, open triangles). After approximately 24 hours, both iodate and iodide began to decline in the wash solution. This result indicates a depletion of the elemental iodine generating formulation from the base polymer coating laid down on the silicone and polyethylene substratum. Elemental iodine was measured within 20 minutes of submerging the tubes in buffer, and at approximately the peak range of iodate and iodide in solution at around 24 hours. The results showed a low of 4 ppm shortly after submersion of the coated devices in the buffer, and a peak level of approximately 30 ppm at the latter peak interval.

The results of these tests demonstrate the feasibility of coating and conferring to prefabricated devices (in this case cannular tubing) microbicidal nascent elemental iodine generating activity. The illustrative device encapsulated the elemental iodine generating formulation within a silicone polymeric base, and then cured it to the outer surface of the prefabricated devices. The outer surface makes contact with fluid upon insertion or placement within an aqueous environment. Therefore, the outer surface is designed to be inserted into body cavities.

EXAMPLE 8

In this example free migration and diffusion of iodine through silicone polymer is demonstrated. Polycarbopol (polyacrylates) and potassium monophosphate, as dry powders, were each separately formulated with iodide and iodate at a 1% by weight composition relative to the silicone elastomer, also made up in 2% sodium iodide and 8% sodium iodate by weight relative to the silicone elastomer. None of the salts were desiccated before slurrying into the silicone polymer to allow for introduction of sufficient water to initiate formation of elemental iodine during the curing process of the polymer base, and thereafter. Each formulation was cast in a plastic tray in a rectangular sheet measuring 8.7 by 11.3 cm and 0.25 cm thick. The catalyst for the silicone elastomer (polydimethylsiloxane with silanol end groups, average molecular weight, 93,000) was dibutyl tin dilaurate. During curing overnight at room temperature, the trays were placed in plastic bags sealed so as to prevent moisture from getting to the trays from the atmosphere, and to retard loss of iodine from the formulated silicone sheets. On the following morning the sheets were seen to be coated with iodine, evident by a light red-brown coloration characteristic of iodine. The presence of iodine was confirmed spectrally in cutting a strip of silicone from the sheets and immersing each in water, and then scanning the sample spectrally for iodine.

To prove iodine was passing freely through the silicone, a strip was cut from each sheet enclosed within the plastic bag and placed outside the bag in the open atmosphere. Under these conditions the iodine was seen to move freely from the silicone strip onto paper strips placed above the cut strips wherein it caused discoloration of the paper. The strips were then placed back into the plastic bag and seen to darken up with the characteristic color of iodine once they were again sealed from the open atmosphere. This cycle was repeated demonstrating the free migration of iodine through silicone once formed from within the interior formulation encapsulated in each sheet.

To further verify the free migration of iodine through silicone, a polymer mix (2% sodium iodide, 8% sodium iodate, 1% potassium monophosphate, undesiccated) was prepared in two 12×75 mm polycarbonate tubes in the silicone elastomer. Upon hardening and storage for 5 days, both showed identical brownish-yellow coloration indicative of iodine formation (de novo), and the coloration was graded. The most intense color was at the bottom of the tube whereas at the very top, exposed to the atmosphere, the color was "sea green" typical of polymer low in iodine content. One tube was split open to expose the polymer uniformly to the atmosphere. Within approximately 30 minutes, the polymer opened to the atmosphere showed a surface coloration as "sea green" with complete loss of its iodine coloration.

A further investigation was undertaken to show that iodine can be produced de novo from the interior of the polymer base and diffuse freely to the exterior. Manufactured silastic tubing, 16 cm in length and 0.5 cm in diameter, was loaded with 0.2 g of a salt mixture ground into a mixture from 0.2 g sodium iodide +0.8 g sodium iodate, and the tubing was sealed into a ring upon then loading the tube with a 0.5% solution of polycarbopol. The silicone ring was rinsed and submerged into a beaker of 30 ml water. Within approximately 5 to 10 min, iodine in the range of 10 to 30 ppm was seen in the water covering the ring, and iodine continued to egress over a 24 hours period with sequential rinsing and refilling of the beaker with fresh water (30 ml). Tests with dyes showed the ring had a tight seal such that iodine was not escaping at the juncture point, but through the silicone wall of the tubing.

EXAMPLE 9

Several prototype hydrogel membranes were produced by (1) preparation of lyophilized hydrogel formulations containing iodide and an oxidant included in the same formulation but lacking substrate (e.g., glucose oxidase and peroxidase), or (2) as sandwich bilayers, in which the iodide and oxidant formulations were first prepared in lyophilized form separately, then compressed together in a hydraulic press to form a bilayer membrane. An example of a single bilayer membrane is illustrated by the preparation of a 1% Noveon AA1, 1% carboxymethylcellulose hydrogel mixture made up in water separated into two equal volumes. A first hydrogel formulation contained 20 mM potassium iodide along with 100 micrograms per ml glucose. In a second hydrogel formulation, glucose oxidase and horseradish peroxidase were added to a final concentration of 100 and 20 micrograms per ml, respectively (specific activities: 100,000 mU per mg and 300,000 mU per mg, respectively). The two hydrogel solutions were then prechilled to about 4° C., then rapidly mixed together within about 5 seconds. The mixture was then immediately poured into an 8.7×11.3 cm plastic tray and frozen at −70° F. While still frozen the sample was then lyophilized for approximately 36 hours under high vacuum after which a sponge-like, slightly tan rectangular membrane was recovered from the tray of approximately 0.3 cm thickness. This membrane was then placed between two metal plates coated with plastic sheeting and subjected to 6000 lbs pressure per square inch resulting in the expression of a thin, paper-like membrane of approximately 9×13 cm and 0.02 cm thick. The membrane was easily cut into various shapes with a pair of scissors, hole punch, or other suitable shearing device, and in this form remained dormant with regard to generating elemental iodine for several months without apparent loss in iodine generating activity. Upon exposure to water, elemental iodine was observed to form within less than 60 seconds, and could be seen to be present in the gel-sol over a period of several hours following hydration of the membrane.

The same two formulations as above were prepared in separate membranes by lyophilizing each hydrogel containing either iodide and glucose, or glucose oxidase and horseradish peroxidase, separately, resulting in the recovery of lyophilized hydrogels of the iodide/glucose and enzyme oxidases in separate membranes. To form a bilayer sandwich, the two membranes were placed one on top of the other and then inserted into the hydraulic press. Upon applying pressure to the sandwiched membranes (6000 lbs per square inch), the two membranes adhered together as a bilayer membrane (one side containing the iodide formulation and the other the enzyme oxidases). This bilayer membrane came out of the press in a rectangular form of approximately 9×12 cm and 0.02 thickness, and was easily cut with scissors or a hole punch into various shapes. Similarly, it proved stable when stored at room temperature for several months without apparent loss in iodine generating activity. The latter was seen to form quickly in less than 60 seconds upon exposure of the bilayer membrane to water.

Varying other formulations such as the preparation of 3% hydroxypropylmethyl cellulose, 1% Noveon AA1 hydrogels made up in 10 mM potassium iodide, 10 mg per ml glucose, and the same hydrogel made up in 100 and 20 microgram per ml glucose oxidase and horseradish peroxidase, respectively, or alternatively made up in 20 mM sodium iodate as the oxidant component, were made and fabricated in the form of pressed membranes using the same techniques, confirming the general principles of this fabrication technique. The final products were all found to be very lightweight, and stable, yet readily produced elemental iodine with wetting of the hydrogel membranes.

EXAMPLE 10

To evaluate retention of formulations within the mechanical-release device in its relaxed (e.g., undistorted, static) state, the delivery device was fabricated as described herein. Specifically, a siliastic tubing was filled with various indicators, then submerged in wash solutions to test for leakage into the external medium bathing the device. A device containing approximately 10 holes per square cm was used in these tests.

In the first experiment, an aqueous solution of toluidine blue (50 ug/ml) was loaded into the inner reservoir, and following closure of the tubing into the ring configuration, the device was rinsed in distilled water, then submerged in 50 ml of 10 mm sodium phosphate buffer, 150 mM NaCl, pH 7.4, placed in a 150 ml glass beaker and left to mix about at the base of the beaker on a rocking shaker over a period of two weeks. The external buffer was examined visually for any presence of the dye egressing from the inner reservoir. None was observed to cross through the perforation holes into the external medium under these conditions. Midway through the two week interval, the device was gently squeezed and contorted. Dye flowed readily into the external medium, but ceased flowing when agitation of the ring was stopped. At this point, the ring was removed from the buffer medium, rinsed under distilled water, and placed back into the beaker on the rocking shaker with a fresh change of buffer. No additional dye was seen to egress from the device until the end of the experiment at which time the ring was once again squeezed and distorted beyond its normal resting state configuration. With this action dye once again egressed from the inner reservoir.

In a second set of experiments, glucose oxidase (D-glucose:oxygen 1-oxidoreductase; EC 1.1.3.4) (1 mg/ml) and horseradish peroxidase (donor:hydrogen-peroxide oxidoreductase; EC 1.11.1.7) (0.5 mg/ml) made up in 10 mM sodium phosphate buffer, 150 mM NaCl, pH 7.4, was loaded into the inner reservoir of the mechanical device. The device ring was closed and rinsed under distilled water. The device was then placed in a beaker containing approximately 20 ml 150 mM potassium iodide and 100 mg/ml glucose made up in distilled water. No formation of elemental iodine, evident by the appearance of the yellow triiodide complex, occurred in the external medium even after leaving the ring submerged in the solution over a period of approximately 8 hours. At the end of the experiment, the ring was squeezed about its outer circumference to distort its shape into an ellipsoid. This latter operation triggered the appearance of triiodide in the external medium (verified as elemental iodine by chloroform extraction and identification of its characteristic violet color in chloroform), indicating that egress of glucose oxidase and horseradish peroxidase had occurred as a result of distortion of the ring, presenting the enzymes formerly contained within the inner reservoir to the substrates in the external medium. This allows for elemental iodine to be formed via oxidation of glucose and subsequent peroxidation of iodide in the external medium.

Both of the foregoing experiments confirm the self-sealing properties, and design, of the mechanical-release device in retaining formulations placed within its inner reservoir, and the elasticity of the pores in resealing and retaining the formulations within the inner reservoir upon cessation of mechanical action on the delivery device.

EXAMPLE 11

Figure 9:
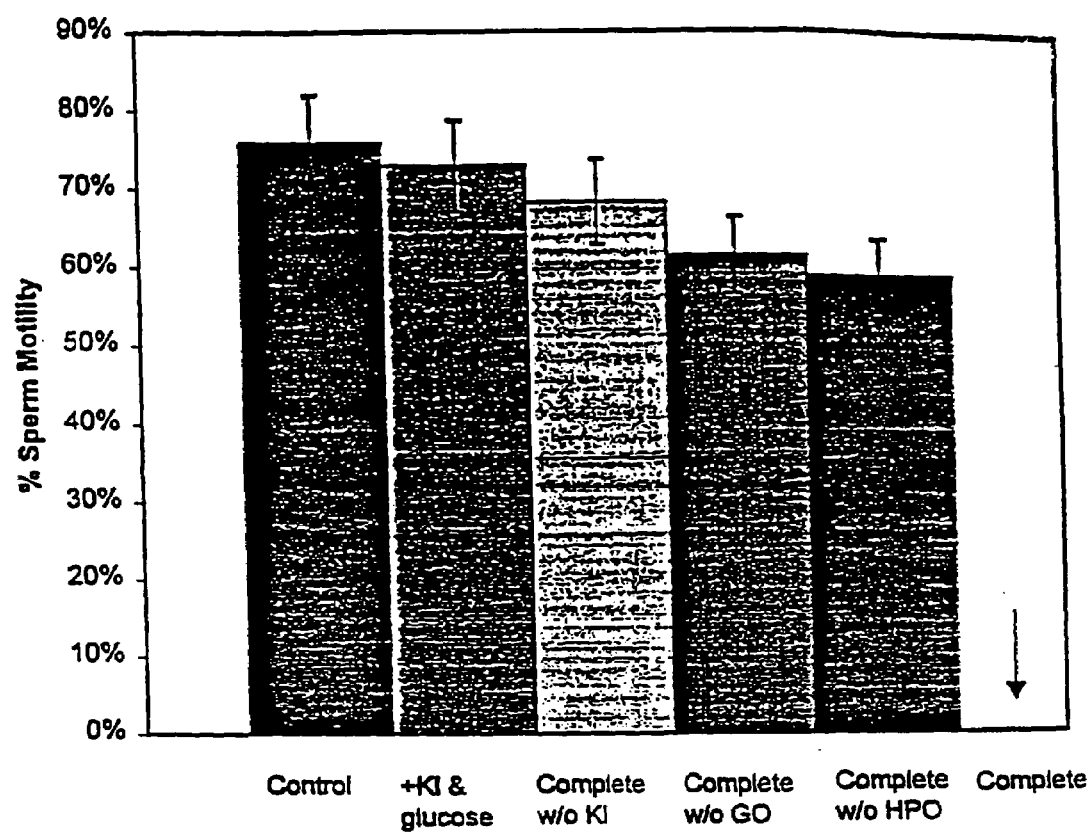
FIG. 9 shows the activity of the spermicidal formulation in immobilizing human sperm. In these experiments glucose oxidase was set at 416 ug/ml, horseradish peroxidase was at 17 ug/ml, iodide was held constant at 63 mM, and glucose was 11.6 mM. Semen was diluted 6-fold in isotonic saline made up in 10 mM sodium phosphate buffer, pH 7.4, and sperm motility scored within 20 seconds of mixing semen with the test reactants. Washing sperm free of the formulation failed to restore sperm motility indicating irreversible immobilization of the sperm. Omission of iodide, or either peroxidase (donor:hydrogen-peroxide oxidoreductase; EC 1.11.1.7) or glucose oxidase (D-glucose:oxygen 1-oxidoreductase; EC 1.1.3.4), from human semen samples resulted in retention of sperm motility. Assays of sperm mobility were based upon WHO standards using the modified Sander-Cramer sperm motility assay. Error bars indicate±1 SD of duplicate determinations of a single donor. Comparable results were obtained on six separate donor specimens obtained on samples of four individual sperm donors. All sperm samples tested met all standard characteristics for assessment of sperm motility (>20×106 sperm/ml, >50% motility and >50% normal forms).

FIG. 9 shows the activity of elemental iodine formed enzymatically through the action of glucose oxidase (D-glucose:oxygen 1-oxidoreductase; EC 1.1.3.4) and horseradish peroxidase (donor:hydrogen-peroxide oxidoreductase; EC 1.11.1.7) on glucose and potassium iodide in immobilizing human sperm. In these experiments glucose oxidase was set at 416 ug/ml, horseradish peroxidase was at 17 ug/ml, iodide was held constant at 63 mM, and glucose was 11.6 mM, all made up in 10 mM sodium phosphate, 150 mM NaCl, pH 7.4 (test reactant mixture). Freshly collected semen was diluted 6-fold in isotonic saline made up in 10 mM sodium phosphate buffer, pH 7.4, and sperm motility scored within 20 seconds of mixing semen with the test reactants. Washing the sperm free of the formulations used in these experiments failed to restore sperm motility indicating irreversible immobilization of the sperm. Omission of iodide, or either horseradish peroxidase or glucose oxidase, from the test reactant to which sperm were added resulted in retention of sperm motility (FIG. 9). Sperm immobilization was complete within 20 seconds in accordance with WHO standards using the modified Sander-Cramer sperm motility assay in scoring test specimens. Error bars indicate±1 SD of duplicate determinations of a single donor. Comparable results were obtained on six separate donor specimens obtained on samples of four individual sperm donors. All sperm samples tested met normal standard characteristics for assessment of sperm motility ($>20\times10^6$ sperm/ml, >50% motility and >50% normal forms).

While the invention has been described in terms of certain preferred embodiments, those skilled in the art will recognize that modifications and improvements may be made to the invention without departing form the scope thereof. For example, while discussed primarily in percarbonate; calcium peroxide, ammonium persulfate, benzoyl peroxide, cumyl hydropeoxide, 3-morpholinosydnonimine hydrochloride (SIN-1), and similar peroxy acid precursors and hydrogen peroxide addition compounds in which hydrogen peroxide is a product formed by spontaneous hydrolysis or solvation of the primary precursor compound. The enzymatic reactants include substrate oxidoreductases illustrated as in the following coupled reactions: glucose+glucose oxidase (D-glucose:oxygen 1-oxidoreductase; EC 1.1.3.4) encapsulated as dry solids within polymer base or with enzyme noncovalently or covalently attached to polymer surface using enzyme immobilization techniques known to those familiar with the art (see below); xanthine (or hypoxanthine)+xanthine oxidase (EC 1.1.3.22) similarly incorporated as in the case of the glucose/glucose oxidase (D-glucose:oxygen 1-oxidoreductase; EC 1.1.3.4) reactants; spermine, putrescine, benzylamine (and related amine substrates) of diamine oxidase; and comparable oxidoreductases in which the substrate serves as an electron donor catalyzing reduction of molecular oxygen to yield hydrogen peroxide either as a direct product or via dismutation of superoxide formed as a precursor of hydrogen peroxide formation. The term benzylamine of diamine oxidase should be understood to mean amine:oxygen oxidoreductase[deaminating] [pyridoxal-containing]; EC 1.4.3.6.

The superoxide, nitric oxide and hydroxyl radical generators include, SIN-1*, S-nitroso-N-acetylpenicillamine (SNAP), and NONOate [N-(2-aminoethyl)-N-(2-hydroxynitrohydrazino)-1,2-ethylenediamine] encapsulated as solids within the polymer base and activated upon wetting of the polymer as generators of NO; xanthine+xanthine oxidase encapsulated as dry solids within the polymer base or with xanthine oxidase noncovalently or covalently attached to the polymer surface, and SIN-1* encapsulated as a solid powder within the polymer base, as generators of superoxide, hydrogen peroxide and hydroxyl radicals. SIN-1 by itself is capable of generating superoxide, hydrogen peroxide, hydroxyl radical, and nitric oxide concomitant with its solvation and subsequent hydrolysis.

Hypohalites can be generated by a polymeric material containing one of the above $H_2O_2$ generators in combination with myeloperoxidase (donor:hydrogen-peroxide oxidoreductase; EC 1.11.1.7) also contained within the polymer base as a dry powder mixture, or with myeloperoxidase noncovalently or covalently attached to the polymer surface. In this formulation, hypochlorous acid is formed upon wetting of the polymer is a body fluid due to the terms of elemental iodine generating formulations, other oxidant generating formulation may be used as well.

We claim:

1. An implantable anti-infective medical device selected from the group consisting of catheters, prostheses, shunts, stents, and leadwires, said device comprising a solid polymeric matrix selected from the group selected from a two component elastomer formulation, room temperature vulcanization elastomers, thermoplastic polymers, and hydrogels, containing within the matrix solid particles of an oxidant-producing component comprising a reducing agent, an oxidizing agent consisting of anhydrous alkali iodine oxide salts, inorganic and organic peracids, iodine pentoxide, an oxidase enzyme, and combinations thereof, that, when wetted, causes the formation of an oxidant and sustained release of the thus-formed oxidant into and about the polymeric matrix so that the matrix serves as an anti-infective reservoir;
   wherein the oxidant is iodine generated at a quantity sufficient so that free-iodine concentration near a surface of the device should reach a level of at least 5 ppm;
   wherein the polymeric matrix is formed from room temperature vulcanization elastomers when the oxidizing agent is selected to be the oxidase enzyme;
   wherein the device further comprises an iodide salt when the oxidizing agent is inorganic and organic peracids or the oxidase enzyme.

2. The anti-infective medical device of claim 1 where the oxidant is elemental iodine.

3. The anti-infective medical device of claim 1 where the oxidant-producing component further comprises a proton donor that, in combination with the reducing agent and the oxidizing agent, forms solid particles dispersed within the polymeric matrix in sufficient amount to provide anti-infective activity to the medical device.

4. The anti-infective medical device of claim 3 where the proton donor is selected from the group consisting of organic acids, inorganic acids, iodine pentoxide, and other acid anhydrides.

5. The anti-infective medical device of claim 4 where the proton donor is selected from the group consisting of perborates and organoperoxy acids.

6. The anti-infective medical device of claim 5 where the proton donor has a concentration of from about 0.01% to about 16% by weight of the polymeric material.

7. The anti-infective medical device of claim 3 wherein the polymeric matrix is the room temperature vulcanization elastomers and where the proton donor is a hydrogen peroxide-generating oxidase enzyme selected from the group consisting of glucose oxidase and diamine oxidase.

8. The anti-infective medical device of claim 7 where the glucose oxidase has a specific activity of from about 2,000 IU/g to about 200,000 IU/g, the diamine oxidase has a specific activity of from about 50 U/g to about 800 IU/g, and the concentration of the glucose oxidase or diamine oxidase is from about 0.01% to about 2.5% by weight of the polymeric material.

9. The anti-infective medical device of claim 7 further comprising a peroxidase enzyme, where the glucose oxidase or diamine oxidase concentration is at least about 0.01% by weight of the polymeric matrix, the peroxidase enzyme is present at a concentration of at least about 0.01% by weight of the polymeric matrix, and the sum concentration of the oxidase and peroxidase enzymes is from about 0.02% to about 2.5% by weight of the polymeric matrix.

10. The anti-infective medical device of claim 1 where the reducing agent is a water soluble iodide salt.

11. The anti-infective medical device of claim 10 where the reducing agent is an alkali iodide salt.

12. The anti-infective medical device of claim 11 where the alkali iodide salt has a concentration of about 0.01% to about 16% by weight of the polymeric matrix.

13. The anti-infective medical device of claim 1 where the oxidizing agent is selected from the group consisting of anhydrous alkali iodate salts, iodine pentoxide, and mixtures thereof.

14. The anti-infective medical device of claim 1 where the polymeric matrix comprises a hydrophobic polymer selected from the group consisting of polyureas, polyurethanes, poly(ethylene/-vinyl acetate), polyvinylchloride, polyesters, polyamides, polycarbonate, polyethylene, polypropylene, polystyrenes, polytetrafluoroethylene, and silicone polymers.

15. The anti-infective medical device of claim 14 where the oxidant is elemental iodine.

16. The anti-infective medical device of claim 14 where the oxidant-producing component further comprises a proton donor that, in combination with the reducing agent and the oxidizing agent, forms solid particles dispersed within the polymeric matrix in sufficient amount to provide anti-infective activity to the medical device.

17. The anti-infective medical device of claim 14 where the reducing agent is a water soluble iodide salt.

18. The anti-infective medical device of claim 17 where the reducing agent is an alkali iodide salt.

19. The anti-infective medical device of claim 18 where the alkali iodide salt has a concentration of about 0.01% to about 16% by weight of the polymeric matrix.

20. The anti-infective medical device of claim 14 where the oxidizing agent is selected from the group consisting of anhydrous alkali iodine oxide salts, iodine pentoxide, inorganic and organic peracids, and combinations thereof.

21. The anti-infective medical device of claim 20 where the oxidizing agent is selected from the group consisting of anhydrous alkali iodate salts, iodine pentoxide, and mixtures thereof.

22. The anti-infective medical device of claim 16 where the proton donor is selected from the group consisting of organic acids, inorganic acids, iodine pentoxide, and other acid anhydrides.

23. The anti-infective medical device of claim 22 where the proton donor is selected from the group consisting of perborates and organoperoxy acids.

24. The anti-infective medical device of claim 23 where the proton donor has a concentration of from about 0.01% to about 16% by weight of the polymeric material.

25. The anti-infective medical device of claim 16 where the polymeric matrix is the room temperature vulcanization elastomers when the proton donor is a hydrogen peroxide-generating oxidase enzyme selected from the group consisting of glucose oxidase and diamine oxidase.

26. The anti-infective medical device of claim 25 where the glucose oxidase has a specific activity of from about 2,000 IU/g to about 200,000 IU/g, the diamine oxidase has a specific activity of from about 50 IU/g to about 800 IU/g, and the concentration of the glucose oxidase or diamine oxidase is from about 0.01% to about 2.5% by weight of the polymeric material.

27. The anti-infective medical device of claim 25 further comprising a peroxidase enzyme, where the glucose oxidase or diamine oxidase concentration is at least about 0.01% by weight of the polymeric matrix, the peroxidase enzyme is present at a concentration of at least about 0.01% by weight of the polymeric matrix, and the sum concentration of the oxidase and peroxidase enzymes is from of about 0.02% to about 2.5% by weight of the polymeric matrix.

28. The anti-infective medical device of claim 1 selected from the group consisting of catheters and prostheses.

29. An implantable anti-infective medical device selected from the group consisting of catheters, prostheses, shunts, stents, and leadwires, comprising a solid polymeric matrix, comprising a solid polymeric matrix selected from the group consisting of room temperature vulcanization elastomers that contain within the matrix solid particles of an oxidant-producing component comprising an iodide salt and an oxidizing agent consisting of substrate oxidoreductases which, when allowed to contact oxidoreductase substrates in body fluids causes the formation of an oxidant and sustained release of the thus-formed oxidant into and about the polymeric matrix so that the matrix serves as an anti-infective reservoir;

wherein the oxidant is iodine generated at a quantity sufficient so that free-iodine concentration near a surface of the device should reach a level of at least 5 ppm.

30. An implantable anti-infective medical device selected from the group consisting of catheters, prostheses, shunts, stents, and leadwires, comprising a solid polymeric matrix selected from the group consisting of thermoplastic polymers and thermosetting polymers, containing within the matrix solid particles of a non-enzyme, oxidant-producing component comprising an oxidizing agent and an iodide salt which, when allowed to contact body fluids, generates an oxidant and sustained release of the thus-formed oxidant into and about the polymeric matrix so that the matrix serves as an anti-infective reservoir, wherein the oxidant is iodine generated at a quantity sufficient so that free-iodine concentration near a surface of the device should reach a level of at least 5 ppm.

* * * * *